United States Patent [19]
Kohn

[11] Patent Number: 5,773,475
[45] Date of Patent: Jun. 30, 1998

[54] ANTICONVULSANT ENANTIOMERIC AMINO ACID DERIVATIVES

[75] Inventor: Harold Kohn, Houston, Tex.

[73] Assignee: Research Corporation Technologies, Inc., Tucson, Ariz.

[21] Appl. No.: 818,688

[22] Filed: Mar. 17, 1997

[51] Int. Cl.$^6$ .................. A61K 31/16; A61K 31/165; C07C 233/05
[52] U.S. Cl. ............. 514/616; 564/155; 564/158
[58] Field of Search ............ 514/616; 564/155, 564/158

[56] References Cited

U.S. PATENT DOCUMENTS

| | | | |
|---|---|---|---|
| 5,378,729 | 1/1995 | Kohn et al. | 514/231.2 |
| 5,654,301 | 8/1997 | Kohn et al. | 514/231.2 |

FOREIGN PATENT DOCUMENTS 0 194 464  9/1986  European Pat. Off. .

OTHER PUBLICATIONS

Anderson et al, J.Am.Chem. Soc., 89:19, pp. 5012–5017, 1967.

Kohn, Harold et al. "Preparation and anticonvulsant activity of a series of functionalized. alph.–heteroatom–substituted amino acids", *J. Med. Chem.*, 1991, 34, 2444–2452.

Kohn, Harold et al. "Marked stereospecificity in a new class of anticonvulsants", *Chemical Abstracts*, 1988, 109, Abstract No. 183045.

Choi, Daeock et al. "Synthesis and Anticonvulsant Activities of N–Benzyl–2–acetamidopropionamide Derivatives", *J. Med. Chem.*, 1996, 39, 1907–1916.

*Primary Examiner*—Shailendra Kumar
*Attorney, Agent, or Firm*—Scully, Scott, Murphy & Presser

[57] ABSTRACT

The present invention is directed to a compound in the R configuration about the asymmetric carbon in the following formula:

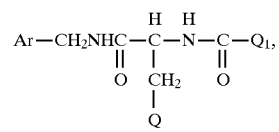

pharmaceutical compositions containing same and the use thereof in treating CNS disorders in animals.

13 Claims, No Drawings

ANTICONVULSANT ENANTIOMERIC AMINO ACID DERIVATIVES

FIELD OF THE INVENTION

The present invention relates to novel enantiomeric compounds and pharmaceutical compositions useful in the treatment of epilepsy and other CNS disorders.

BACKGROUND OF THE INVENTION

The predominant application of anticonvulsant drugs is the control and prevention of seizures associated with epilepsy or related central nervous system disorders. Epilepsy refers to many types of recurrent seizures produced by paroxysmal excessive neuronal discharges in the brain; the two main generalized seizures are petit mal, which is associated with myoclonic jerks, akinetic seizures, transient loss of consciousness, but without convulsion; and grand mal which manifests in a continuous series of seizures and convulsions with loss of consciousness.

The mainstay of treatment for such disorders has been the long-term and consistent administration of anticonvulsant drugs. Most drugs in use are weak acids that, presumably, exert their action on neurons, glial cells or both of the central nervous system. The majority of these compounds are characterized by the presence of at least one amide unit and one or more benzene rings that are present as a phenyl group or part of a cyclic system.

Much attention has been focused upon the development of anticonvulsant drugs and today many such drugs are well known. For example, the hydantions, such as phenytoin, are useful in the control of generalized seizures and all forms of partial seizures. The oxazolidinediones, such as trimethadione and paramethadione, are used in the treatment of non-convulsive seizures. Phenacemide, a phenylacetylurea, is one of the most well known anticonvulsants employed today, while much attention has recently been dedicated to the investigation of the diazepines and piperazines. For example, U.S. Pat. Nos. 4,002,764 and 4,178,378 to Allgeier, et al. disclose esterified diazepine derivatives useful in the treatment of epilepsy and other nervous disorders. U.S. Pat. No. 3,887,543 to Nakanishi, et al. describes a thieno [2,3-e][1,4]diazepine compound also having anticonvulsant activity and other depressant activity. U.S. Pat. No. 4,209,516 to Heckendorn, et al. relates to triazole derivatives which exhibit anticonvulsant activity and are useful in the treatment of epilepsy and conditions of tension and agitation. U.S. Pat. No. 4,372,974 to Fish, et al. discloses a pharmaceutical formulation containing an aliphatic amino acid compound in which the carboxylic acid and primary amine are separated by three or four units. Administration of these compounds in an acid pH range are useful in the treatment of convulsion disorders and also possess anxiolytic and sedative properties.

U.S. Pat. No. 5,378,729 to Kohn, et al. discloses compounds and pharmaceutical compositions having central nervous system (CNS) activity which are useful in the treatment of epilepsy and other CNS disorders having the following general formula:

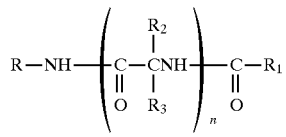

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group, or electron donating group.

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z—Y wherein $R_2$ and $R_3$ may be unsubstituted or substituted with at least one electron withdrawing group or electron donating group;

Z is O, S, S $(O)_a$, $NR_4$, $PR_4$ or a chemical bond;

Y is hydrogen, lower alkyl, aryl, aryl lower alkyl, lower alkenyl, lower alkynyl, halo, heterocyclic, or heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$, $PR_4SR_7$, $NR_4PR_5R_6$, $PR_4NR_5R_7$,

$R_4$, $R_5$ and $R_6$ are independently hydrogen, lower alkyl, aryl, aryl lower alkyl, lower alkenyl, or lower alkynyl, wherein $R_4$, $R_5$ and $R_6$ may be unsubstituted or substituted with an electron withdrawing group or an electron donating group, $R_7$ is $R_6$, $COOR_8$ or $COR_8$, $R_8$ is hydrogen, lower alkyl, or aryl lower alkyl, and the aryl or alkyl group may be unsubstituted or substituted with an electron withdrawing group or an electron donating group and n is 1–4 and a is 1–3.

Unfortunately, despite the many available pharmacotherapeutic agents, a significant percentage of the population with epilepsy or related disorders are poorly managed. Moreover, none of the drugs presently available are capable of achieving total seizure control, and most have disturbing side effects. Toxicities may appear upon repeated dosing that are not apparent with acute administration. Because many drugs which require chronic administration ultimately place an extra burden on the liver, including for example, liver enzyme induction or oxidative metabolism that may generate reactive species, many anticonvulsants have associated therewith liver toxicity.

Research is continuing in this area to find better and more effective anticonvulsant agents, especially for long term treatment (chronic administration). Obviously, the ideal drug is one that has high pharmacological activity, minimal side effects and is relatively non-toxic and safe to the animal that is being treated. More specifically, the ideal anticonvulsant drug is one that satisfies the following four criteria: (1) has a high anticonvulsant activity, (expressed as a low $ED_{50}$); (2) has minimal neurological toxicity, (as expressed by the median toxic dose ($TD_{50}$)), relative to its potency; (3) has a maximum protective index (sometimes known as selectivity or margin of safety), which measures the relationship between the doses of a drug required to produce undesired and desired effects, and is measured as the ratio between the median toxic dose and the median effective dose ($TD_{50}/ED_{50}$); and (4) is relatively safe as measured by the median lethal close ($LD_{50}$) relative to its potency and is non-toxic to the animal that is being treated, e.g., it exhibits minimal adverse effects on the remainder of the treated animal, its organs, blood, its bodily functions, etc. even at high concentrations, especially during long term chronic administration of the drug. Thus, for example, it exhibits minimal, i.e., little or no liver toxicity. Although not as critical in short term or acute administration of an anti-convulsant, since the animal may tolerate some low levels of toxicity, the fourth criteria outlined above is extremely important for an anti-convulsant which is to be taken over a long period of time (chronic administration) or in high dosage. It may be the most important factor in determining which anti-convulsant to administer to a patient, especially if chronic dosing is required. Thus, an anti-convulsant agent which has a high anti-convulsant activity, has minimal neurological toxicity and maximal P.I. (protective index) may unfortunately exhibit such toxicites which appear upon repeated high levels of administration. In such an event, acute dosing of the drug may be considered, but it would not be used in a treatment regime which requires chronic administration of the anti-convulsant. In fact, if an anti-convulsant is required for repeated dosing in a long term treatment regime, a physician may prescribe an anti-convulsant that may have weaker activity relative to a second anti-convulsant, if it exhibits relatively low toxicity to the animal. An anti-convulsant agent which meets all four criteria is very rare.

However, the present inventor has found such a group of compounds that is generally potent, exhibit minimal neurological toxicity, has a high protective index and is relatively non-toxic to the body organs, including the liver upon multiple dosing.

SUMMARY OF THE INVENTION

Accordingly, the present invention is directed to N-benzyl-2-acetamido propionamide derivatives in the R configuration having the formula:

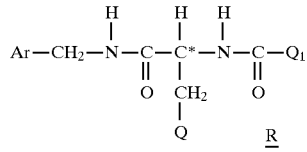

wherein

Ar is aryl which is unsubstituted or substituted with halo;

Q is lower alkoxy; and $Q_1$ is $CH_3$.

The present invention contemplates employing the compound of Formula I in a pharmaceutical composition. Moreover, the administration of an effective amount of the present compounds in their pharmaceutically acceptable forms provides an excellent regime for the treatment of epilepsy, nervous anxiety, psychosis, insomnia, and other related central nervous disorders.

These drugs exhibit high anti-convulsant activity, minimal neurological toxicity, high P.I. and minimal toxicity. These anti-convulsants are utilized in a treatment regime requiring acute dosing, and especially chronic dosing thereof to the patient.

As shown hereinbelow, the compounds of the present invention exhibit minimal effects on liver, which is in contrast to other anti-convulsant compounds.

DETAILED DESCRIPTION OF THE INVENTION

As used herein the term "alkoxy" refers to an O-alkyl group attached to the main chain through an oxygen bridge, wherein alkyl is as defined hereinabove. The alkoxy groups are lower alkoxy groups containing one to six carbon atoms, and more preferably, one to three carbon atoms. The most preferred alkoxy groups are propoxy, isopropoxy, ethoxy and especially methoxy.

The term "aryl", when used alone or in combination, refers to a phenyl group which is unsubstituted or substituted with halo.

The term halo includes fluoro, chloro, bromo, iodo and the like. The preferred halo is fluoro.

It is preferred that Q in the compound of formula I is alkoxy having 1–3 carbon atoms. The most preferred alkoxy group is propoxy, isopropoxy, ethoxy and especially methoxy.

The Ar group as defined herein, is phenyl, which may be unsubstituted or substituted as defined herein. It is most preferred that the aryl group, i.e., phenyl, is unsubstituted or substituted with only one halo group. It is more preferred that if substituted, the halo substituent is in the para or meta position. It is even more preferred that the phenyl group is unsubstituted.

Examples of the compounds of the present invention include:

(R)-N-Benzyl-2-acetamido-3-methoxy propionamide, (R)-N-(3-Fluorobenzyl)-2-acetamido-3-methoxypropionamide, (R)-N-(4-Fluorobenzyl)-2-acetamide-3-methoxypropionamide, (R)-N-Benzyl-2-acetamido-3-ethoxy propionamide.

As indicated by the asterisk in formula I, the compounds of the present invention contain at least one asymmetric carbon. The stereochemistry of the asymmetric carbon at the asterisk is in the R configuration. The inventor has found that the R stereoisomer at the asymmetric carbon at the asterisk is significantly more efficacious than the corresponding S enantiomer or a racemic mixture thereof.

It is preferred that the compound of the present invention be substantially pure, i.e., substantially free from impurities. It is most preferred that the compounds of the present invention be at least 75% pure (w/w) and more preferably greater than about 90% pure (w/w) and most preferably greater than about 95% pure (w/w).

It is also preferred that the compounds of the present invention be substantially enantiomerically pure, i.e., substantially free from the corresponding S isomer. It is more preferred that the compounds of the present invention contain at least 90% (w/w) R stereoisomer, and most preferably greater than about 95% (w/w) in the R stereoisomer. Thus, the present invention contemplates compounds having at most about 10% S isomer (w/w), and even more preferably less than about 5% S isomer (w/w).

The compounds of the present invention in the R form are prepared by art recognized techniques from commercially available starting materials.

An exemplary procedure is outlined in Scheme 1 hereinbelow:

Scheme 1

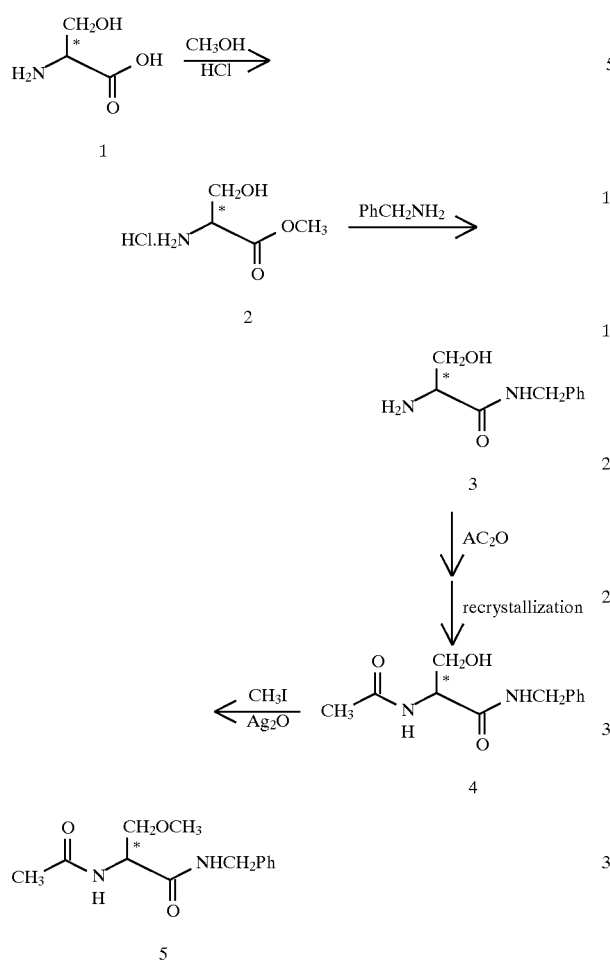

A D serine molecule (1) is esterified under acylation conditions with an alcohol, such as acidic methanol, to provide the corresponding ester (2). 2 is reacted with $ArCH_2NH_2$, such as benzylamine, under acylation conditions to form the corresponding amide (3). Acylation of the free amino group, with an acylating derivative of

such as acetic acid, or lower alkyl ester of acetic acid, or acetic anhydride provides the hydroxymethyl derivative, i.e.,

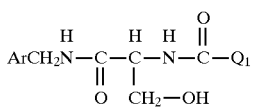
(4)

The enantiopurity of 4 was determined by techniques known in the art, including melting point, optical rotation and $^1H$ NMR upon addition of an organic acid in the R-configuration, such as R(−)- mandelic acid. Crystallization of 4 was repeated until the desired enantiopurity thereof was achieved. The product of 4 is converted to the ether under Williamson conditions by reacting it with QX, wherein Q is as defined herein above and X is good leaving groups, such as OTs, OMs, or halide (e.g., $CH_3I$) and the like in the presence of base (e.g., $Ag_2O$) to form the product (5) having Formula I.

Another variation is depicted in Scheme 2.

Scheme 2

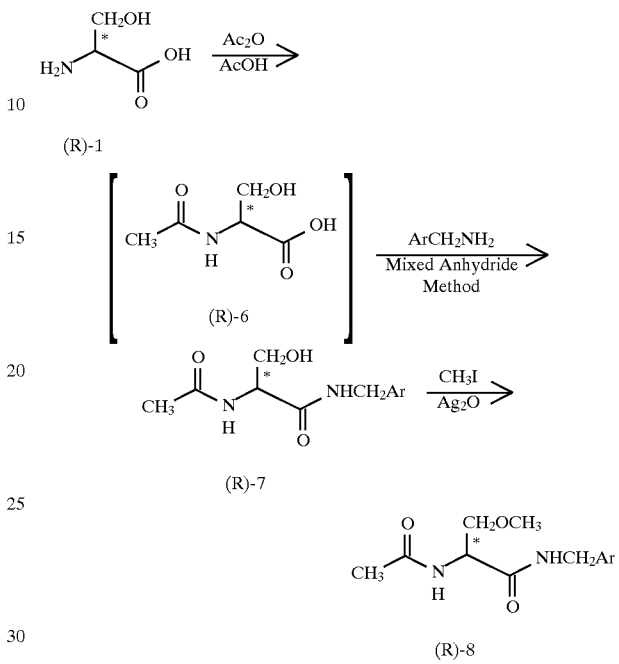

For example, beginning with D-serine (1), treatment with an acylating derivative of acetic acid such as acetic anhydride in acetic acid, gives the corresponding amide 6 which is then reacted with $ArCH_2NH_2$ under mixed anhydride coupling reaction conditions, as described by Anderson, et al., in JACS, 1967, 89, 5012–5017, the contents of which are incorporated herein by reference, to give the corresponding compound of the formula:

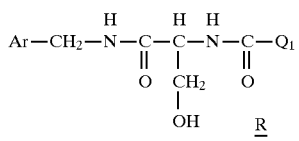

e.g., 7. Alkylation of this R-product in the presence of base under Williamson conditions, such as methyl iodide in $Ag_2O$, provides a product of Formula I (8).

An alternative route is depicted in Scheme 3.

Scheme 3

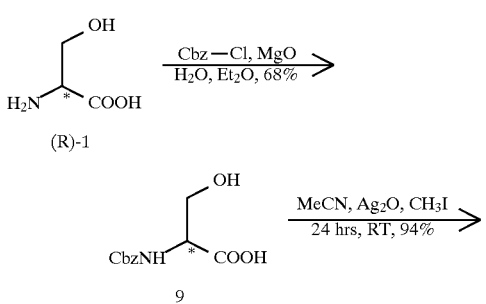

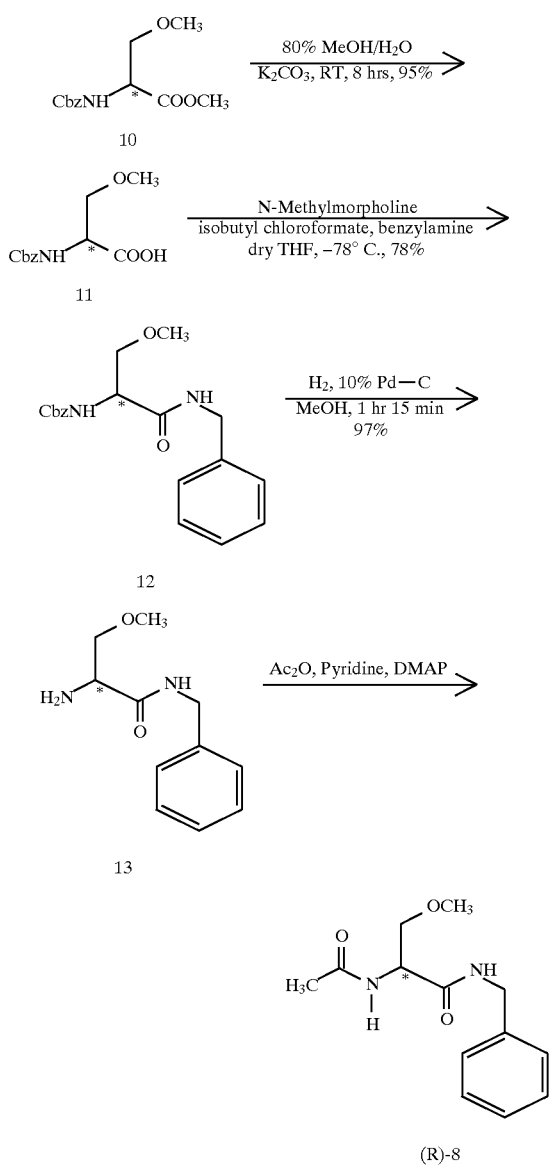

D Serine (1) is protected with a N-protecting group known in the art, by standard techniques. Thus, for example, it is reacted with carbobenzoxy chloride (CBZ-cl, benzyl chloroformate) generating the N-protected CBZ-D-serine adduct 9. The protected serine adduct is converted to the corresponding ether under Williamson conditions by reacting it with QX wherein Q and X are defined hereinabove (e.g., $CH_3I$) in the presence of base (e.g., $Ag_2O$) to form an ether 10. Under these conditions, the acid is also esterified. Subsequent hydrolysis of the ester group in 10 permits amide coupling with $ArCH_2\ NH_2$ using amide coupling methodology (e.g., mixed anhydride 1,1' Carbonyldiimidazole) to give the amide 12. Deprotection of the N-protecting group provide the free amine 13 which is then reacted with an acylating agent such as acetic anhydride in base, (e.g., pyridine) to provide the product (R)-8.

If necessary, in any of the procedures described hereinabove, the optical purity of the product may be enhanced by further separation of the S emantiomer from the R emantiomer, by standard techniques known in the art, such as chiral chromatography using a standard chiral support known in the art.

Alternatively, in any of the procedures provided hereinabove, a racemic D serine may be utilized as the starting material. Following the procedures in any of the schemes outlined hereinabove would provide the racemic mixture, which can be resolved into the R isomer by standard techniques known in the art such as chiral chromatography.

The active ingredients of the therapeutic compositions and the compounds of the present invention exhibit excellent anticonvulsant activity when administered in amounts ranging from about 1 mg to about 100 mg per kilogram of body weight per day. This dosage regimen may be adjusted by the physician to provide the optimum therapeutic response. For example, several divided doses may be administered daily or the dose may be proportionally reduced as indicated by the exigencies of the therapeutic situation. A decided practical advantage is that the active compound may be administered in an convenient manner such as by the oral, intravenous (where water soluble), intramuscular or subcutaneous routes.

The active compound may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly, dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 5 to about 1000 mg. Expressed in proportions, the active compound is generally present in from about 1 to about 750 mg/ml of carrier. In the case of compositions containing supplementary active ingredients, the dosages are determined by reference to the usual dose and manner of administration of the said ingredients.

Unless indicated to the contrary, percentages are by weight.

As used herein, the term lower alkyl refers to an alkyl group containing 1–6 carbon atoms which may be straight chained or branched.

For a better understanding of the present invention reference is made to the following description and examples.

GENERAL METHODS

Melting points were determined with a Thomas Hoover melting point apparatus and are uncorrected. Infrared spectra (IR) were run on Perkin-Elmer 1330, 283 and a Mattson Genesis spectrometer and were calibrated against the 1601 $cm^{-1}$ bond of polystyrene. Absorption values are expressed in wave-numbers ($cm^{-1}$). Proton ($^1H$ NMR) and carbon ($^{13}C$ NMR) nuclear magnetic resonance spectra were taken on Nicolet NT-300 and General Electric QE-300 NMR instruments. Chemical shifts ($\delta$) are in parts per million (ppm) relative to $Me_4Si$ and coupling constants (J values) are in hertz. All chemical ionization mass spectral investigations were conducted on Finnegan MAT TSQ-70 instrument. Microanalyses were provided by Atlantic Microlab Inc. (Norcross, Ga). Thin layer chromatography was performed on precoated silica gel GHLF microscope slides (2.5×10 cm; Analtech No. 21521).

EXAMPLE 1

(R)-N-Benzyl-2-Acetamide-3-methoxypropionamide

Hydrochloric acid (8.00 g, 219.4 mmol) was passed into MeOH (250 mL) and then D-Serine (20.00 g, 190.3 mmol) was added. The reaction solution was heated at reflux (18 hours), benzylamine (81.6 mL, 761 mmol) was added and then the reaction was heated for an additional eighteen hours. The solvent was removed under reduced pressure, the insoluble salts filtered, and the excess benzylamine was removed under high vacuum (Kugelrohr). The residue was dissolved in water (100 mL), and the product was extracted with $CHCl_3$ (8×200 mL). The organic layers were combined, dried ($Na_2SO_4$), and the solvent was removed under reduced pressure. The residue was triturated with $Et_2O$ (150 mL) and filtered to give 10.0 g (27%) of the product R-enriched N-benzyl 2-aminohydracrylamide, as a white solid: mp 74°–78° C.; $[\alpha]_D^{23}$ (c=1, MeOH)=1.6°, $R_f$ 0.30 (10% MeOH—$CHCl_3$); $^1H$ NMR (DMSO-$d_6$) $\delta1.87$ (br s, $NH_2$), 3.23 (t, J=5.4 Hz, CH), 3.39–3.55 (m, $CH_2OH$), 4.28 (d, J=5.7 Hz, $NHCH_2$) 4.76 (t, J=5.4 Hz, $CH_2OH$), 7.18–7.32 (m, 5PhH), 8.34 (t J=5.7 Hz, NH), $^{13}C$ NMR (DMSO-$d_6$) 41.8 ($NHCH_2$), 56.9 (CH), 64.3 ($CH_2OH$), 126.6 ($C_4'$), 127.0 ($2C_2'$ or $2C_3'$), 128.1 ($2C_2'$ or $2C3'$), 139.5 $C_1'$), 173.3 (C(O)NH) ppm, MS (+Cl) (rel intensity), 195 ($M^+$+1, 53), 117 (100), Mr(+Cl) 195.113 56 ($M^+$+1) (calcd. for $C_{10}H_{15}N_2O_2$, 195.11335).

To a stirred methylene chloride suspension (100 ml) of R enriched N-benzyl-2-aminohydracrylamide (10.00 g, 51.5 mmol) was added acetic anhydride (5.8 mL, 61.8 mmol), and the reaction suspension was stirred at room temperature (1 hour). The solvent was removed under reduced pressure to give a white solid. The product was triturated with $Et_2O$ (250 mL) to give 7.60 g (62%) of enriched R-N-benzyl-2-acetamidohydracrylamide as a white solid. The reaction product was recrystallized (2×) using EtOH to give 3.50 g (29%) of the R-N-benzyl-2-acetamidohydracrylamide mp 148°–149° C.; $[\alpha]_D^{23}$ (c=1, MeOH)=+22.4°; Rf 0.40 (10% MeOH—$CHCl_3$); IR (KBr) 3295, 3090, 2964, 1642, 1533, 1376, 1281, 1051, 705 cm; $^1H$ NMR (DMSO-$d_6$) δ1.86 (s, C(O)$CH_3$), 3.57 (dd, J=5.7, 5.7 Hz, $CH_2OH$), 4.25–4.31(m, CH), 4.27 (d, J=5.7 Hz, $NHCH_2$), 4.92 (t, J=5.7 Hz, $CH_2OH$), 7.18–7.32 (m, 5 PhH) 7.94 (d, J=7.8Hz, NH), 8.38 (t, J=5.7 H, NH), addition of excess R-(–) mandelic acid to a $CDCl_3$ solution of R-N-benzyl 2-acetamidohydracrylamide prepared hereinabove gave only one signal for the acetyl methyl protons; $^{13}C$ NMR (DMSO-$d_6$) 22.7 (C(O)$CH_3$), 42.0 ($CH_2NH$), 55.6 (CH), 61.8($CH_2OH$), 126.7 ($C_4'$), 127.0 ($2C_2'$ or $2C_3'$), 128.2 ($2C_2'$ or $2C_3'$), 139.4 ($C_1'$), 169.5 (C(O)$CH_3$ or C(O)NH), 170.3 (C(O)$CH_3$ or C(O)NH) ppm; MS (+Cl) rel intensity) 237 ($M^++1$, 100), 219(8); $M_r$(+Cl) 237.12388 [$M^++1$] (calcd for $C_{12}H_{17}N_2O_3$ 237.12392); Anal ($C_{12}H_{16}N_2O_3$), C,H,N.

To a stirred acetonitrile solution (300 mL) of (R)-N-benzyl-2-acetamidohydroacrylamide (2.36 g, 10 mmol) was successively added $Ag_2O$ (11.59 g, 50 mmol) and methyl iodide (6.2 mL, 100 mmol) at room temperature. The reaction mixture was stirred at room temperature for 4 days. The insoluble salts were filtered, and the solvents were removed in vacuo to give a white solid. The residue was filtered with $Et_2O$ (100 mL) to give 2.20 g (88%) of the above-identified product.

mp 143°–144° C.; $[\alpha]_D^{23}$ (c=1, MeOH)=+16.4°; Rf0.47 (10% MeOH—$CHCl_3$); IR (KBr) 3289, 3086, 2923, 2876, 2819, 1636, 1547, 1138, 695 $cm^{-1}$; $^1H$ NMR (CDCl$_3$) δ2.04 (s, C(O)$CH_3$), 3.38 (s, $OCH_3$), 3.43 (dd, J=7.8, 9.0 Hz, CHH'$OCH_3$), 3.82 (dd, J=4.2, 9.0 Hz, CHH'$OCH_3$), 4.48(d, J=6.0 Hz, $NHCH_2$), 4.51–4.57 (m,CH), 6.44 (br d, J=5.4 Hz, NH), 6.75 (br s, NH), 7.25–7.37 (m, 5 PhH), addition of excess (R)-(–)-mandelic acid to a $CDCl_3$ solution of (R)-18 gave only one signal for the acetyl methyl and ether methyl protons; $^{13}C$ NMR (CDCl$_3$) 23.2 (C(O)$CH_3$), 43.5 ($CH_2NH$), 52.4 (CH), 59.1 ($OCH_3$), 71.7 ($CH_2OCH_3$), 127.4 ($C_4'$), 127.5 ($2C_2'$ or $2C_3'$) , 128.7 (2C2' or $2C_3'$), 137.9 ($C_1'$), 169.9 (C(O)$CH_3$ or C(O)NH), 170.3 (C(O)$CH_3$ or C(O)NH) ppm; MS (+Cl) (rel intensity) 251 ($M^++1$, 100), 219(6); Mr (+Cl)251.139 76 [$M^++1$] (calcd for $C_{13}H_{19}N_2O_3$ 251.139 57); Anal. ($C_{13}H_{18}N_2O_3$) C, H, N.

EXAMPLE 2

Another Synthesis of (R)-N-Benzyl 2-Acetamide-3-methoxy propionamide (a) Improved Synthesis of (R)-N-Benzyl 2-Acetamidohydracrylamide To a stirred AcOH (20 mL) suspension of D-serine (5.26 g, 50 mmol) was added $Ac_2O$ (4.7 mL, 50 mmol), and then the reaction suspension was stirred at room temperature (24 hours). The ACOH was removed in vacuo to give an oily residue, and then THF (150 mL) was added to the residue. The THF suspension was cooled to –78° C. under $N_2$ and 4-methylmorpholine (11.0 mL, 100 mmol) was added. After stirring for two minutes, isobutyl chloroformate (13.0 mL, 100 mmol) was added leading to the precipitation of a white solid. The reaction was allowed to proceed for two additional minutes and then benzylamine (10.4 mL, 100 mmol) was added at –78° C. The reaction mixture was allowed to stir at room temperature (30 minutes) and the 4-methylmorpholine hydrochloride salt was filtered. The organic layer was concentrated in vacuo. The product was purified by flash column chromatography on $SiO_2$ gel (10% MeOH—$CHCl_3$) to give 3.89 g (33%) as a white solid mp 147°–148° C., $[\alpha]_D^{23}$ (C=1, MeOH)=+21.70; $^1H$ NMR (DMSO-$d_6$) δ1.86 (s, C(O) $CH_3$), 3.57 (dd, J=5.1, 5.1 Hz, $CH_2O$) 4.27–4.31 (m, $CH_2NH$, CH), 4.90 (t, J=5.1 Hz, OH), 7.20–7.31 (m, 5 PhH), 7.93, (d, J=8.1 Hz, NH), 8.37 (t, J=6.0 Hz, NH), addition of excess (R)-(–)-mandelic acid to a $CDCl_3$ solution of the product of (a) gave only one signal for the acetyl methyl protons.

(b) (R)-N-Benzyl-2-Acetamide-3-methoxypropionamide

To the compound prepared in (a) (1.42 g, 6 mmol) in a stirred solution (300 ml) of $CH_3CN$ was successively added $Ag_2O$ (6.95 g, 30 mmol) and methyl iodide (3.7 mL, 60 mmol) and stirred at room temperature for 4 days. The insoluble salts were filtered and the solvent was removed in vacuo to give a white solid. The white solid was triturated with $Et_2O$ (100 mL) to given 1.30 g (87%) of the above-identified compound: mp 143°–144° C., $[\alpha]_D^{23}$ (c=1, MeOH)=+16.0°; $^1H$ NMR (CDCl$_3$) δ2.04 (s, C(O)$CH_3$), 3.38(s, $OCH_3$), 3.44 (dd, J=7.5, 9.0 Hz, CH $H^1$ $OCH_3$), 3.81 (dd, J=4.2, 9.0 Hz, CHH'$OCH_3$), 4.48 (d, J=5.7 Hz, $NHCH_2$), 4.52–4.58 (m, CH), 6.46 (br d, J=5.7 Hz, NH), 6.78 (br, s, NH), 7.25–7.37 (m, 5 Ph H), addition of excess (R)-(–)-mandelic acid to a $CDCl_3$ solution of the above-identified compound gave only one signal for the acetyl and ether methyl protons.

EXAMPLE 3

R-N-(3-Fluorobenzyl)2-Acetamide-3-Methoxypropionamide (a) R-N-(3-Fluorobenzyl)-2-Acetamide-hydracrylamide Utilizing the procedure of Example 2(a) with the following amounts of D-serine (5.26 g, 50 mmol), $Ac_2O$ (5.7 mL, 60 mmol), 4-methylmorpholine (11.0 mL, 100 mmol), isobutyl chloroformate (13.0 mL, 100 mmol) and substituting 3-fluorobenzylamine (11.8 mL, 100 mmol) for benzylamine, gave 4.20 g (33%) of the above compound as a white solid after purification: mp 137°–138° C.; $[\alpha]_D^{23}$ (c=1, MeOH)=+20.8°; Rf0.32 (10% MeOH—$CHCl_3$); IR (KBr) 3282, 3101, 2944, 1636, 1542, 1252, 1050, 779, 690 $cm^{-1}$; $^1H$ NMR (DMSO-$d_6$) δ1.87 (s,C(O)$CH_3$), 3.56–3.63 (m, $CH_2OH$), 4.29 (d, J=6.0 Hz, $CH_2NH$), 4.25–4.30 (m, CH), 4.95 (t, J=5.4 Hz, $CH_2OH$), 7.00–7.09 (m, 3 ArH), 7.29–7.30 (m, 1 ArH), 7.97 (d, J=8.1 Hz, NH), 8.44 (t, J=6.0 Hz, NH), addition of excess (R)-(–)-mandelic acid to a $CDCl_3$ solution of this product gave only one signal for the acetyl methyl portions; $^{13}C$ NMR (DMSO-$d_6$) 22.7 (C(O) $CH_3$), 41.6 ($CH_2N$), 53.4 (CH), 61.7 ($CH_2$ OH), 113.3 (d, $J_{CF}$=20.0 Hz, ($C_2'$ or $C_4'$), 113.6 (d, $J_{CF}$=20.7 Hz, $C_2'$ or $C_4'$), 122.9 ($C_6'$), 130.1 (d, $J_{CF}$=8.2 Hz, $C_5'$), 142.6 (d, $J_{CF}$=7.0 Hz, $C1_1'$), 162.3 (d, $J_{CF}$=241.4 Hz, $C_3'$), 169.6 (C(O)$CH_3$ or C(O)NH), 170.5 (C(O)$CH_3$ or C(O)NH) ppm; MS (+Cl) (rel. intensity) 255 ($M^++1$, 100); $M_r$(+Cl) 255.113 54 [$M^++$1] (calcd. for $C_{12}H_{16}FN_2O_3$ 255.114 50); Anal. ($C_{12}H_{15}FN_2O_3$) C, H, N.

(b) (R)-(N-3-Fluorobenzyl)-2-Acetamide-3-methoxypropionamide

To the product of (a) (2.54 g, 10 mmol) in a stirred $CH_3CN$ solution was successively added $Ag_2O$ (11.59 g, 50 mmol) and MeI (6.2 mL, 100 mmol) at room temperature. The reaction mixture was stirred at room temperature for 2 days. The insoluble salts were filtered and the solvent was removed in vacuo to give a white solid which was triturated with Et$_2$O (100 mL) to give a crude product of the above identified compound. The product was further purified by flash chromatography on SiO$_2$ gel (10% MeOH—CHCl$_3$) to give 2.00 g (75%) of the above-identified compound: mp 150°–151° C.; $[\alpha]_D{}^{23}$ (c=1, MeOH)=+16.5° C.; R$_f$ 0.50 (10% MeOH—CHCl$_3$); IR (KBr) 3287, 3072, 2928, 2883, 1634, 1548, 1256, 1142, 785 cm$^{-1}$; $^1$H NMR (CDCl$_3$) δ2.05 (s, C(O)CH$_3$), 3.40 (s, OCH$_3$), 3.44–3.47 (m, CHH'OCH$_3$), 3.81–3.85 (m, CHH'OCH$_3$), 4.41–4.50 (m, NHCH$_2$), 4.53–4.59 (m, CH), 6.42 (br s, NH), 6.81 (br s, NH), 6.93–7.05 (m, 3 PhH), 7.26–7.31 (m, 1 PhH); addition of excess (R)-(−)-mandelic acid to a CDCl$_3$ solution of the above identified compound gave only one signal for the acetyl methyl protons and ether methyl protons; $^{13}$C NMR (DMSO-d$_6$) 22.8 (C(O)CH$_3$), 42.7 (CH$_2$N), 52.6 (CH), 58.9 (OCH$_3$), 72.0 (CH$_2$OCH$_3$), 114.0 (d, $J_{CF}$=21.5 Hz, C$_{2'}$ and C$_{4'}$), 122.7 (C$_6$), 129.9 (d, $J_{CF}$=7.7 Hz, C$_{5'}$), 140.6 (d, $J_{CF}$=6.8 Hz, C$_{1'}$), 162.9 (d, $J_{CF}$=244.4 Hz, C$_{3'}$), 170.2 (C(O)CH$_3$ or C(O)NH), 170.5 (C(O)CH$_3$ or C(O)NH) ppm; MS (+Cl) (rel. intensity) 269 (M$^+$+1, 100); Mr (+Cl) 269.129 31 [M$^+$+1] (calcd for C$_{13}$H$_{18}$FN$_2$O$_3$ 269.130 15); Anal. (C$_{13}$H$_7$FN$_2$O$_3$) C, H, N.

EXAMPLE 4

(R)-N-(4-Fluorobenzyl)2-Acetamido-3-Methoxypropanamide (a) (R)-N-(4-Fluorobenzyl)2-Acetamido-hydracrylamide Utilizing the procedure of Example 2(a) with the following amounts of D-serine (5.26 g, 50 mmol), Ac$_2$O (5.7 mL, 60 mmol), 4-methylmorpholine (11.0 mL, 100 mmol), and isobutyl chloroformate (13.0 mL, 100 mmol) and substituting 4-fluorobenzylamine (11.8 mL, 100 mmol) for benzylamine, the above-identified compound was prepared as a white solid after purification (4.08 g, 32%); mp: 169°–170° C.; $[\alpha]_D{}^{23}$ (c=1, MeOH)=+17.6°; R$_f$0.31 (10% MeOH—CHCl$_3$); IR (KBr) 3289, 3101, 3071, 2936, 1632, 1565, 1543 1508, 1214, 1053, 814 cm$^-$; $^1$H NMR (DMSO-d$_6$) δ1.86 (s, C(O)CH$_3$), 3.56 (6, J=5.4 Hz, CH$_2$OH), 4.25 (d, J=6.0 Hz, CH$_2$NH), 4.25–4.29 (m, CH), 4.91 (t, J=5.4 Hz, CH$_2$OH), 7.08–7.14 (m, 2C$_{2'H}$), 7.25–7.29 (m, 2C$_{3'H}$), 7.93 (d, J=7.8 Hz, NH), 8.39 (d, J=6.0 Hz, NH), addition of excess (R)-(−)-mandelic acid to a CDCl$_3$ solution of the above-identified compound gave only one signal for the acetyl methyl protons; $^{13}$C NMR (DMSO-d$_6$) 22.7 (C(O)CH$_3$), 41.3 (CH$_2$N), 55.3 (CH), 61.7 (CH$_2$OH), 114.8 (d, $J_{CF}$=21.8 Hz, 2C$_{3'}$), 128.9 (d, $J_{CF}$=8.0 Hz, 2C$_{2'}$), 135.6 (C$_{1'}$), 161.1 (d, $J_{CF}$=240.1 Hz, C$_{4'}$), 169.4 (C(O)CH$_3$ or C(O)NH), 170.3 (C(O)CH$_3$ or C(O)NH) ppm; MS (+Cl) (rel. intensity) 255 (M$^+$+1, 100); Mr(+Cl) 255.113 60 [M$^+$+1] (calcd for C$_{12}$H$_{16}$FN$_2$O$_3$ 255.114 50); Anal. (C$_{12}$H$_{15}$FN$_2$O$_3$.0.2H$_2$O) C, H, N.

(b) R-N-(4-Fluorobenzyl)2-Acetamido-3-methoxypropanamide

Following the procedure of Example 3(b) to the product of Example 4(a) (2.54 g, 10 mmol) in a stirred CH$_3$CN solution (300 mL) was successively added) Ag$_2$O (11.59 g, 50 mmol) and MeI (6.2 mL, 100 mmol) at room temperature and then stirred for 7 days. The insoluble salts were filtered, and the solvent was removed in vacuo to given a white solid. The white solid was triturated with Et$_2$O (100 mL) to give a crude product. The crude product was further purified by flash column chromatography (10% MeOH—CHCl$_3$) to give 2.00 g (75%) of the above product; mp: 144°–145° C.; $[\alpha]_D{}^{23}$ (c=1, MeOH)=+12.00; R$_f$0.52 (10% MeOH—CHCl$_3$); IR (KBr) 3281, 3102, 3072, 2959, 1632, 1547, 1513, 1223, 1100 cm$^{-1}$; $^1$H NMR (CDCl$_3$) δ2.04 (s, C(O)CH$_3$), 3.38 (s, OCH$_3$), 3.39–3.46 (m, CHH'OCH$_3$), 3.80–3.84 (m, CHH'OCH$_3$), 4.44 (br d, J=5.4 Hz, CH$_2$NH), 4.48–4.56 (m, CH), 6.42 (br s, NH) 6.76 (br s, NH), 6.99–7.05 (m, 2 PhH), 7.21–7.31 (m, 2 PhH), addition of excess (R)-(−)-mandelic acid to a CDCl$_3$ solution of the above-identified product gave only one signal for the acetyl methyl portions and ether methyl portions, $^{13}$C NMR (CDCl$_3$) 22.9 (C(O)CH$_3$), 42.6 (CH$_2$N), 52.5 (CH), 58.9 (OCH$_3$), 72.0 (CH$_2$OCH$_3$), 115.3 (d, $J_{CF}$=22.0 Hz, 2C$_{3'}$), 129.0 (d, $J_{CF}$=6.9 Hz, 2C$_{2'}$), 133.7 (C$_{1'}$) 161.9 (d, $J_{CF}$=245.3 Hz, C$_{4'}$), 170.1 (C(O)CH$_3$ or C(O)NH), 170.4 (C(O)CH$_3$ or C(O)NH) ppm; MS (+Cl) (rel. intensity) 269 (M$^+$+1, 100); Mr (+Cl) 269.129 66 [M$^+$+1] (calcd for C$_{13}$H$_{18}$FN$_2$O$_3$ 269.130 15); Anal. (C$_{13}$H$_{17}$FN$_2$O$_3$) C, H, N.

EXAMPLE 5

N-Benzyl 2-Acetamide-3-Methoxypropionamide (a) Cbz-(D) Serine (9)

D-Serine (5 g) was dissolved in water (85 mL). To this was added MgO (6 g), and ethyl ether (40 mL). The mixture was cooled in an ice bath to 0° C. To this ice-cold mixture was added slowly, dropwise benzylchloroformate (95%, 11 mL). Upon complete addition, the mixture was stirred at 0° C. (2 h) and then allowed to spontaneously warm to room temperature. Stirring was continued for an additional 30 minutes. The mixture was filtered and the filtrate washed with ethyl ether (2×25 mL). The aqueous layer was separated and cooled in an ice bath to 0° C. The pH of this ice-cold aqueous layer was carefully adjusted to 3.0 using 5N HCl. The acidified solution was stored in a refrigerator overnight. The white crystalline solid product was. isolated by filtration, and dried in vacuo. The filtrate was extracted with ethylacetate (2×50 mL). The combined ethyl acetate extracts were dried (Na$_2$SO$_4$), filtered and evaporated in vacuo to obtain additional amounts of the white crystalline product. Total product obtained was 7.51 g (68%): mp 118°–120° C.

(b) Methyl-2-(Carbobenzyloxyamino)-3-Methoxypropionate (10)

To a solution of 9 (1.72 g, 7.21 mmol) in actonitrile (150 mL) was added methyl iodide (10.23 g, 72.1 mmol, 4.5 mL) and silver(I)oxide (8.4 g, 36 mmol) and the mixture was stirred in the dark at room temperature for 24 hours. The insoluble salts and excess silver oxide were removed by filtration and the filtrate was evaporated in vacuo to obtain an oily residue which was subjected to flash column chromatography (silica gel and 5% MeOH—CHCl$_3$) to obtain pure 10 as a pale yellow oil (1.81 g, 94%): R$_f$ (10% MeOH/CHCl$_3$) 0.75.

(c) 2-(Carbobenzyloxyamino)-3-Methoxypropionic Acid (11)

Compound 10 (0.58 g) was dissolved in 80% aqueous methanol (3.0 mL). To this solution was added anhydrous K$_2$CO$_3$ (0.5 g) and the reaction mixture was stirred at room temperature (8 hours). The methanol was evaporated in vacuo and the residue suspended in water (50 mL). The aqueous suspension was washed with ethyl ether (2×25 mL) and then acidified to pH 3.0 using 5N HCl. The acidified aqueous phase was extracted with ethyl acetate (3×25 mL). The ethyl acetate extracts were combined, dried ($Na_2SO_4$), filtered, and evaporated in vacuo to obtain pure 11 as a clear viscous oil (0.52 g, 95%): $R_f$ 0.30 (10% $MeOH/CHCl_3$).

(d) N-Benzyl 2-(Carbobenzyloxyamino)-3-Methoxypropionamide (12)

A solution of 11 (0.52 g, 2.04 mmol) in dry tetrahdrofuran (10 mL) was cooled to −78° C. in a dry ice-acetone bath under a $N_2$ atmosphere. To this was added via a dry syringe 4-methylmorpholine (0.34 mL, 3.06 mmol). After stirring for 5 minutes, isobutyl chloroformate (0.4 mL, 3.06 mmol) was added via dry syringe and then the mixture stirred for 5 minutes. This was followed by the addition of benzylamine (0.32 mL, 3.06 mmol). After stirring at −78° C. for 5 minutes, the reaction was allowed to warm to room temperature, and stirring was continued at room temperature (30 min). The hydrochloride salt of 4-methyl morpholine was removed from the reaction by filtration. The clear filtrate was evaporated in vacuo and the residue was triturated with ethyl ether (5.0 mL). The white crystalline product obtained was isolated by filtration after washing with small amounts of ether and air-dried (0.55 g, 78%): mp 112°–114° C., $R_f$ 0.6 (10% $MeOH/CHCl_3$)

(e) N-Benzyl-2-Amino-3-Methoxypropionamide (13)

To a solution of 12 (122.8 mg, 0.36 mmol) in methanol (2.0 mL) was added 10% Pd—C (11 mg) and the mixture stirred at room temperature in the presence of $H_2$ gas for 75 min. Celite was added to the reaction mixture and the catalyst was removed by filtration. The clear filtrate was evaporated in vacuo to give pure 13 as a clear viscous oil (72 mg, 97%): $R_f$ 0.30 (5% $MeOH/CHCl_3$).

(f) N-Benzyl-2-Acetamido-3-Methoxypropionamide

To a solution of 13 (0.20 g, 0.98 mmol) in dry THF (2.0 mL) is added pyridine (0.086 g, 1.08 mmol), and then acetic anhydride (0.2 g, 1.96 mmol) is added dropwise. The reaction is stirred at room temperature for 18 hours. The solvent is evaporated in vacuo and the residue purified by flash column chromatography to obtain the above compound as the R isomer.

COMPARATIVE EXAMPLE 1

Preparation of N-Acetyl-D,L-alanine-N'-benzylamide

Acetic anhydride (2.20 g, 0.022 mol) was slowly added to a methylene chloride solution (30 mL) of D,L-alanine-N-benzylamide (3.80 g, 0.021 mol) and allowed to stir at room temperature (3 h). The mixture was then successively washed with $H_2O$ (15 mL), dried ($Na_2SO_4$) and concentrated in vacuo. The residue was recrystallized from $CH_2Cl_2$.

Yield: 2.50 g (54%). mp 139°–141° C.

$^1H$ NMR (DMSO-$d_6$): δ1.22 (d, J=7.1 Hz, 3H), 1.84 (s,3H), 4.04–4.50 (m,3H), 7.26 (s,5H), 8.11 (br d, J=7.3 Hz, 1H), 8.42 (br t, J=6 Hz, 1H).

$^{13}C$ NMR (DMSO-$d_6$): 18.2, 22.4, 41.9, 48.2, 126.5, 126.9, 128.1 139.4, 168.9, 172.4 ppm.

IR ($CHCl_3$) 3440, 3300, 3005, 1660, 1515 $cm^{-1}$.

Mass spectrum (CI mode), m/e: 221 (P+I); mol wt. 220.1208 (calculated for $C_{12}H_{16}N_2O_2$, 220.1212).

COMPARATIVE EXAMPLES 2 AND 3

Preparation of N-Acetyl D and L-amino acid N-benzylamides

General procedure: The D or L amino acid amide (11 mmol) was dissolved in dichloromethane (15 mL) and then acetic anhydride (1.23 g, 1.40 mL, 12 mmol) was added dropwise. The solution was stirred at room temperature (18 h) and then concentrated to dryness. The residue was crystallized from chloroform/hexane.

COMPARATIVE EXAMPLE 2

N-Acetyl-D-alanine-N'-benzylamide

Yield: 1.36 g (56%). mp 139°–141° C. $[\alpha]_D^{23}$=+36.2 (c 2.5, MeOH).

$^1H$ NMR (80 MHz, DMSO-$d_6$): δ1.25 (d, J=7.1 Hz, 3H), 1.86 (s, 3H), 4.04–4.50 (m, 1H), 4.30 (d, J=6.0 Hz, 2H), 7.26 (s, 5H), 8.09 (d, J=7.3 Hz, 1H), 8.40 (t, J=6.0 Hz, 1H).

$^{13}C$ NMR (80 MHz, DMSO-$d_6$): 18.3, 22.5, 42.0, 48.4, 126.6, 127.0 (2C), 128.2 (2C), 139.4, 169.2, 172.5 ppm.

IR (KBr): 3290, 1635 (br), 1540, 1455, 700, 695 $cm^{-1}$.

Mass spectrum, m/e (relative intensity): 221 (30), 114 (20), 106 (40), 91 (80), 87 (100), 77 (5), 72 (20), 65 (5).

Elemental analysis calculated for $C_{12}H_{16}N_2O_2$ 65.42% C; 7.34% H; 12.72% N. Found 65.31% C; 7.28% H; 12.63% N.

COMPARATIVE EXAMPLE 3

N-Acetyl-L-alanine-N'-benzylamide

Yield: 1.11 g (46%). mp 139°–142° C. $[\alpha]_D^{23}$−35.3 (c 2.5, MeOH). $^1H$ NMR (80 MHz, DMSO-$d_6$): δ1.23 (d, J=7.2 Hz, 3H), 1.86 (s, 3H), 4.26–4.35 (m, 1H), 4.29 (d, J=5.8 Hz, 2H), 7.22–7.33 (s,5H), 8.10 (d, J=7.4 Hz, 1H), 8.42 (t, J=5.8 Hz, 1H).

$^{13}C$ NMR (80 MHz, DMSO-$d_6$): 18.3, 22.6, 42.0, 48.4, 126.7, 127.0 (2C), 128.3 (2C) 139.5, 169.2, 172.6 ppm.

IR (KBr): 3290, 1635 (br), 1545, 1450, 700, 695 $cm^{-1}$.

Mass spectrum, m/e (relative intensity): 221 (40), 114 (40), 106 (80), 106 (80), 91 (75), 87 (100), 77 (5), 72 (15), 65 (5).

Elemental analysis calculated for $C_{12}H_{16}N_2O_2$ 65.42% C; 7.34% H; 12.72% N. Found 65.58% C; 7.32% H; 12.43% N.

COMPARATIVE EXAMPLE 4

Preparation of D,L-2-Acetamido-N-benzyl-2-methoxyacetamide

To a methanolic solution (180 mL) of methyl 2-acetamide-2-methoxyacetate (8.73 g, 54 mmol) was rapidly added benzylamine (8.68 g, 8.80 mL, 81 mmol) and then the mixture was stirred at 50° C. (3 days) during which time a beige precipitate appeared. The solvent was removed in vacuo and the resulting precipitate was recrystallized from tetrahydrofuran (2x) to given 7.67 g (32%) of the desired product as beige crystals: Rf 0.35 (95:5 chloroform/methanol). mp 145°–146° C.

$^1H$ NMR (300 MHz, $CDCl_3$): δ2.06 (s, $CH_3CO$), 3.37 (2,$CH_{3O)}$, 4.40–4.35 (m, $CH_2$), 5.52 (d, J=8.7 Hz, CH), 7.12 (d, J=8.7 Hz, NH), 7.20–7.40 (m, Ph, NH).

$^{13}C$ NMR (300 MHz, $CDCl_3$): 23.03 ($CH_3CO$), 43.51 ($CH_2$), 55.84 ($CH_{3O)}$, 78.94 (CH), 127.62 ($C_4$"), 127.70 ($2C_2$" or $2C_3$"), 128.70 ($2C_2$ or $2C_3$'), 137.45 ($C_1$"), 166.91 ($COCH_3$), 171.57 (CONH) ppm.

IR (KBr): 1260, 1825 (br), 1550, 1505, 1435, 1390, 1370, 1230, 1120, 1050 935, 890, 690 cm$^{-1}$.

Mass spectrum, m/e (relative intensity): 237 (1), 205 (2), 177 (2), 163 (4), 146 (1), 134 (1), 121 (2), 106 (26), 102 (98), 91 (95), 77 (13), 61 (100). Elemental analysis calculated for $C_{12}H_{16}N_2O_3$ 61.00% C; 6.83% H; 11.86% N. Found 60.91% C; 6.85% H; 11.66% N.

COMPARATIVE EXAMPLES 5–7

Synthesis of Unsubstituted and Substituted-a-Acetamido-N-benzyl-2-furanacetamides General Procedure 4-Methylmorpholine (1 equiv) was added to a solution of a-acetamido-2-furanacetic acid (1 equiv) in dry tetrahydrofuran (75 mL/10 mmol) at −10° to −15° C. under $N_2$. After stirring (2 min.), isobutyl chloroformate (1 equiv) was added leading to the precipitation of a white solid. The reaction was allowed to proceed for 2 additional minutes and then a solution of the substituted benzylamine (1 equiv) in tetrahydrofuran (10 mL/10 mmol) was added over 5 min. at −10° to −15° C. The reaction mixture was allowed to stir at room temperature for 5 min. and then the 4-methylmorpholine hydrochloride salt filtered. The organic layer was concentrated in vacuo, and the residue was triturated with ethyl acetate, and the remaining white solid filtered. Concentration of the ethyl acetate layer led to additional amounts of the white solid. The desired product was purified by either recrystallization or flash chromatography of the combined solid material.

COMPARATIVE EXAMPLE 5

(D,L)-α-Acetamido-N-benzyl-2-furanacetamide

Benzyl amine (0.27 g, 2.56 mmol) and racemic α-acetamido-2-furanacetic acid (0.47 g, 2.56 mmol) gave the desired compound. The product was recrystallized from ethyl acetate to give a white solid.

Yield: 0.46 g (65%) $R_f$ 0.30 (98:2 chloroform/methanol). mp 177°–178° C.

$^1$H NMR (DMSO-$d_6$) δ1.90 (s, $CH_3$), 4.31 (d, J=6.0 Hz, $CH_2$), 5.58 (d, J=8.1 Hz, CH), 6.27–6.33 (m, $C_3H$), 6.40–6.44 (m, $C_4H$), 7.20–7.36 (m, 5 PhH), 7.60–7.64 (m, $C_5H$), 8.57 (d, J=8.1 Hz, NH), 8.73 (t, J=6.0 Hz, NH).

COMPARATIVE EXAMPLE 6

(D)-(−)α-Acetamido-N-benzyl-2-furanacetamide

Starting with D-α-acetamido-2-furanacetic acid (2.45 g, 13.38 mmol) and benzylamine (1.43 g, 13.38 mmol), the desired product was obtained. Yield: 2.54 g (70%). The product was further recrystallized from ethyl acetate to give the title compound.

Yield: 2.30 g mp 196°–197° C. $[\alpha]^{26}$D[c=1, MeOH]= 78.30. Addition of R(−)-mandelic acid to a $CDCl_3$ solution the product gave only one signal for the acetamide methyl protons. Mass spectrum, m/e (relative intensity) 272 (M+, 2), 184 (2), 165 (2), 140 (8), 139 (88), 138 (34), 97 (46), 96 (100), 91 (63).

Elemental analysis: calculated: 66.16% C; 5.92% H; 10.29% N. Found: 66.09% C; 6.01% H; 10.38% N.

COMPARATIVE EXAMPLE 7

(L)-(+)-α-Acetamido-N-benzyl-2-furanacetamide

L-α-acetamido-2-furanacetic acid (2.83 g, 15.46 mmol) and benzylamine (1.65 g, 15.4 mmol) gave 3.80 g of the enriched desired product. $^1$H NMR analysis with R(−)-mandelic acid showed that it was greater than 80% enriched in the title compound. The pure L-enantiomer was obtained by recrystallization from absolute ethanol.

Yield: 1.60 g. mp 196°–197° C. $[\alpha]^{26}$D[c=1, MeOH]=+ 79.0°.

Mass spectrum, m/e (relative intensity) 273 ($M^+$+1,3) 229 (2), 214 (2), 184 (1), 165 (7), 157 (4), 140 (33), 139 (100), 138 (95), 97 (98), 96 (100), 91 (98).

Elemental analysis: calculated: 66.16% C; 5.92% H; 10.29% N. Found: 65.89% C; 5.86% H; 10.42% N.

COMPARATIVE EXAMPLE 8

Synthesis of N-Benzyl 2-Acetamidohydracrylamide

To an anhydrous THF solution (400 mL) of methyl-α-acetamido-N-benzylmalonamate (14.4 g, 54.5 mmol) was successively added dry LiCl (4.62 g, 109 mmol), $NaBH_4$ (4.13 g, 109 mmol) and EtOH (200 mL). The reaction mixture was stirred at room temperature (5h). The suspension was concentration in vacuo. After continuous extraction (12h) of the product using $CHCl_3$ (1000 mL) and $H_2O$ (250 mL), the organic layer was collected, dried ($Na_2SO_4$), and removed in vacuo to give a crude white solid. The crude product was triturated with $Et_2O$ (500 mL) to give 11.45 g (89%) of the above compound: mp 201°–203° C.; $R_f$0.40 (10% MeOH—$CHCl_3$); IR (KBr) 3287, 3085, 2969, 2859, 1648, 1552, 1456, 1055, 697 cm$^-$; $^1$H NMR (DMSO-$d_6$) 51.88 (s, C(O)$CH_3$), 3.59 (dd, J=5.7 Hz, 5.7 Hz, $CH_2O$), 4.19–4.35 (m, $CH_2NH$, CH), 4.92 (t, J=5.7 Hz, OH), 7.10–7.40 (m, 5 PhH), 7.94 (d, J=5.7 Hz, NH), 8.38 (t, J=5.7 Hz, NH); $^{13}$C NMR (DMSO-$d_6$) 22.2 (C(O)$CH_3$), 41.6 ($CH_2N$), 54.9 (CH), 61.3 ($CH_2OH$), 126.2 ($C_{4'}$), 126.5 ($2C_{2'}$ or $2C_{3'}$), 127.7 ($2C_{2'}$ or $2C_{3'}$), 138.9 ($C_{1'}$), 169.1 (C(O)$CH_3$ or C(O)NH), 169.9 (C(O)$CH_3$ or C(O)NH) ppm; MS (+Cl) (relative intensity) 237 ($M^+$+1, 100), 219 (9); Mr(+Cl) 237.123 88 [$M^+$+1] (calcd for $C_{12}H_{17}N_2O_3$ 237.123 92); Anal. ($C_{12}H_{16}N_{2l\ o3}$) C, H, N.

COMPARATIVE EXAMPLE 9

Synthesis of N-Benzyl 2-Acetamido-3-methoxypropionamide(racemic mixture)

To an $CH_3CN$ solution (500 mL) of the product of Comparative Example 8 (2.36 g, 10 mmol) was successively added $Ag_2O$ (11.59 g, 50.0 mmol) and $CH_3l$ (6.23 mL, 100 mmol) at room temperature and then the reaction mixture was stirred at room temperature (4 d). The insoluble salts were filtered, and the solvent was removed in vacuo to give a white solid. The residue was triturated with $Et_2O$ (50 mL) to give 2.10 g (84%) of the above-identified compound: mp 121°–122° C.; $R_f$0.47 (10% MeOH—$CHCl_3$); IR (KBr) 3290, 3087, 2924, 2878, 2820, 1637, 1548, 1139, 695 cm$^{-1}$; $^1$H NMR ($CDCl_3$) δ2.04 (s,C(O)$CH_3$), 3.38 (s, $OCH_3$), 3.43 (dd, J=7.8, 9.0 Hz, CHH'$OCH_3$), 3.82 (dd, J=4.2, 9.0 Hz, CHH'$OCH_3$), 4.48 (d, J=6.0 Hz, $NHCH_2$), 4.51–4.57 (m,CH), 6.43 (br d, J=5.4 Hz, NH), 6.74 (br s, NH), 7.25–7.37 (m, 5 PhH); $^{13}$C NMR ($CDCl_3$) 23.2 (C(O)$CH_3$), 43.5 ($CH_2N$), 52.4 (CH), 59.1 ($OCH_3$), 71.7 ($CH_2OCH_3$), 127.4 ($C_{4'}$ and $2C_{2'}$ or $2C_{3'}$), 128.7 ($2C_{2'}$ or $2C_{3'}$), 137.8 ($C_{1'}$), 170.0 (C(O)$CH_3$ or C(O)NH), 170.3 (C(O)$CH_3$ or C(O)NH) ppm; MS (+Cl) (relative intensity) 251 ($M^+$+1, 100), 219 (100); Mr(+Cl) 251.139 39 [$M^+$+1] (calcd for $C_{13}H_{19}N_2O_3$ 251.139 57); Anal. ($C_{13}H_{18}N_2O_3$) C, H, N.

COMPARATIVE EXAMPLE 10

(S)-N-Benzyl 2-Acetamidohydracrylamide

To a stirred AcOH (20 mL) suspension of L-serine (2.63 g, 25 mmol) was added $Ac_2O$ (2.5 mL, 26.3 mmol) and then the reaction suspension was stirred at room temperature (24h). The AcOH was removed *in vacuo* to given an oily residue, and then THF (150 mL) was added to the residue. The THF suspension was cooled to −78° C. under $N_2$ and 4-methylmorpholine (5.5 mL, 50 mmol) was added. After stirring (2 min.), isobutyl chloroformate (6.5 mL, 50 mmol) was added leading to the precipitation of white solid. The reaction was allowed to proceed for two additional minutes and then benzylamine (5.5 mL, 50 mmol) was added at −78° C. The reaction mixture was allowed to stir at room temperature (30 min.) and then the 4-methylmorpholine hydrochloride salt was filtered. The organic layer was concentrated *in vacuo*. The product was purified by flash column chromatography on $SiO_2$ gel (10% MeOH—$CHCl_3$) to given 2.20 g (37%) of the above product as a white solid: mp 146°–147° C.; $[\alpha]_D^{23}$ (c=1, MeOH)=−21.50; $^1H$ NMR (DMSO-$d_6$) δ1.86 (s, C(O)$CH_3$), 3.57 (dd, J=5.1 Hz, 5.1 Hz, $CH_2$O), 4.25–4.32 (m, $CH_2$NH, CH), 4.91 (t, J=5.1 Hz, OH), 7.20–7.33 (m, 5 PhH), 7.93 (d, J=8.1 Hz, NH), 8.37 (t, J=5.7 Hz, NH), addition of excess (R)-(−)mandelic acid to a $CDCl_3$ solution of the above-identified compound gave only one signal for the acetyl methyl protons.

COMPARATIVE EXAMPLE 11

(S)-N-Benzyl 2-Acetamido-3-methoxypropionamide

To a stirred $CH_3CN$ solution (300 mL) of the compound produced in Comparative Example 10 (1.18 g, 5 mmol) was successively added $Ag_2O$ (5.80 g, 25 mmol) and MeI (3.1 mL, 10 mmol) at room temperature. The reaction mixture was stirred at room temperature (4 d). The insoluble salts were filtered, and the solvent was removed in vacuo to give a white solid. The white solid was triturated with $Et_2O$ (100 mL) to give 1.00 g (80%) of the above-identified compound: mp 143°–144° C. $[\alpha]^{23}D$ (c=1, MeOH)=−16.4°; $^1H$ NMR ($CDCl_3$) δ2.03 (s, C(O)$CH_3$), 3.38 (s, $OCH_3$), 3.43 (dd, J=7.5, 9.0 Hz, CHH'$OCH_3$), 3.81 (dd, J=4.2, 9.0 Hz, CHH'$OCH_3$), 4.47 (d, J=5.7 Hz, $NHCH_2$), 4.52–4.59 (m,CH), 6.48 (br d, J=6.0 Hz, NH), 6.81 (br s, NH), 7.25–7.37 (m, 5 Ph), addition of excess (R)-(−)-mandelic acid to a $CDCl_3$ solution of the above-identified compound gave only one signal for the acetyl methyl and ether methyl protons.

COMPARATIVE EXAMPLE 12

(R)-N-Benzyl 2-Acetamidohydracylamide

This compound was prepared in accordance with the procedures described in Examples 1 and 2.

COMPARATIVE EXAMPLE 13

N-Acetyl-D,L-phenylglycine-N-benzylamide

This compound was prepared in accordance with the procedure described in U.S. Pat. No. 5,378,729, the contents of which are incorporated by reference. The D,L-phenylglycine amide (11 mmol) was dissolved in dichloromethane (15 mL) and then acetic anhydride (1.23 g, 1.40 mL, 12 mmol) was added dropwise. The solution was stirred at room temperature (4–6h) and then concentrated to dryness. The residue was recrystallized from chloroform/hexane.

Yield: 2.05 g (66%) mp 202°–203° C.

$^1H$ NMR (DMSO-$d_6$) : δ1.91 (s, 3H) , 4.27 (d, J=5.6 Hz, 2H), 5.50 (d, J=7.9 Hz, 1H), 7.21 (s, 5H), 7.36 (s, 5H), 8.38–8.86 (m, 2H).

$^{13}C$ NMR (DMSO-$d_6$): 22.3, 42.0, 56.3, 126.6 (2C), 127.0, 127.1 (2C), 127.4 (2C), 128.1 (2C), 138.9, 139.0, 168.9, 169.9 ppm.

IR (KBr): 3020, 1635, 1580, 1540, 1450, 1265, 745, 690 $cm^{-1}$.

Mass spectrum, m/e (relative intensity): 283(20), 264(21), 149(100), 131(20), 118(34), 106(92), 91(70), 79(56), 77(54), 65(45), 51(37).

Elemental analysis Calculated for $C_{17}H_{18}N_2O_2$ 72.31% C; 6.44% H; 9.92% N. Found 72.49% C; 6.47% H; 9.89% N.

The compounds of the present invention are useful for the treatment of central nervous disorders, such as epilepsy, nervous anxiety , psychosis, insomnia and the like in animals, e.g., mammals, such as man, in need thereof. They exhibit excellent anti-convulsant activity, and of course and can thus be administered for short term treatment. Moreover, the compounds of the present invention have the added advantage of being useful in drug regimes for long-term treatment. The compounds of the present invention are substantially non-toxic, exhibiting minimal toxicity, if any, to the treated animal, as shown below in the pharmacology section.

PHARMACOLOGY

Compounds were screened for anticonvulsant activity in both male albino Carthworth Farms No. 1 mice (ip route) and male albino Sprague Dawley rats [oral (po) route]. Activity was established using the electrical (maximal electroshock or MES) test. In the MES test, a drop of electrolyte solution with anesthetic (0.5% butacaine hemisulfate in 0.9% sodium chloride) was used in the eyes of the animals prior to positioning the corneal electrodes and delivery of current. A 60 cycle alternating current was administered for 0.2 sec. in both species, 50 mA in mice and 150 mA in rats. Protection endpoints were defined as the abolition of the hind limb tonic extensor component of the induced seizure. In mice, effects of compounds on forced spontaneous motor activity were determined using the rotorod test. The inability of animals to maintain their balance for 1 min. on a 1 inch diameter knurled rod at 6 rpms in 3 successive trials demonstrated motor impairment. Normally under these conditions, mice maintain their balance almost indefinitely. In rats, motor impairment is assessed by observing for overt evidence of ataxia, abnormal gait and stance, and/or loss of placing response and muscle tone. In the mouse identification screening study all compounds were given at three dose levels (30, 100, 300 mg/kg) and two time periods (0.5 hours, 4 hours). Typically, in the MES seizures test one animal was tested at 30 mg/kg and 300 mg/kg, and three animals at 100 mg/kg. In the rotorod toxicity test four animals were tested at 30 mg/kg, and 300 mg/kg, and eight animals at 100 mg/kg. If activity was found at 30 mg/Kg, then lower dosages were used to find the $ED_{50}$ values.

The quantitative determination of the median effective ($ED_{50}$) and toxic doses ($TD_{50}$) was conducted at previously calculated times of peak effect. Groups of at least eight animals were tested using different doses of test compound until at least two points were determined between 100 and 0% protection and minimal motor impairment. The dose of candidate substance required to produce the defined endpoint in 50% of the animals in each test and the 95% confidence interval was calculated.

TABLE 1

Physical and Pharmacological Data for Functionalized N-Benzyl
2-Acetamidopropionamide Stereoisomers of the formula $ArCH_2NHC(O)CH(R^2)NHC(O)CH_3$

| No. | Stereohem. | $R^2$ | Ar | m p[a] | mice (ip)[b] MES,[c] $ED_{50}$ | tox,[d] $TD_{50}$ | PI[e] | rat (po)[f] MES,[c] $ED_{50}$ | tox,[d] $TD_{50}$ | PI[e] |
|---|---|---|---|---|---|---|---|---|---|---|
| Comp. Ex. 1 | (R, S) | $CH_3$ | Ph | 138–139 | 76.5 [1] (66.6–89.0 | 454 [0.5] (417–501) | 5.9 | 24.2 [1] (32.0–71.8) | —[h] | >20.8 |
| Comp. Ex. 2 | (R) | $CH_3$ | Ph | 139–141 | 54.8 [0.5] (50.3–59.7) | 2.14 [0.5] (148–262) | 3.9 | 28.4 [4] (22.4–35.0) | —[h] | >35.2 |
| Comp. Ex. 3 | (S) | $CH_3$ | Ph | 139–142 | 548 [0.5] (50.3–59.7) | 841 [0.5] (691–954) | 1.5 | —[j] | —[j] | j |
| Comp. Ex. 9 | (R, S) | $CH_2OCH_3$ | Ph | 121–122 | 8.3 [0.5] (7.9–9.8) | 42.9 [0.25] (38.1–46.8) | 5.2 | 3.8 [2] (2.9–5.5) | 386.8 [1] (316.0—514.6) | 101.8 |
| Ex. 1, 2 | (R) | $CH_2OCH_3$ | Ph | 143–144 | 4.5 [0.5] (3.7–5.5) | 26.8 [0.25] (25.5–28.0) | 6.0 | 3.9 [0.5] (2.6–6.2) | >500 [0.5] | >128.2 |
| Comp. Ex. 11 | (S) | $CH_2OCH_3$ | Ph | 143–144 | >100, <300 | >300 | | >30 | >30 | j |
| Comp. Ex. 8 | (R, S) | $CH_2OH$ | Ph | 201–203 | >100, 300 | >300 | | —[j] | —[j] | j |
| Comp. Ex. 12 | (R) | $CH_2OH$ | Ph | 148–149 | 53.4 [2] (37.5–67.3) | >500 [2] | >9.4 | —[j] | —[j] | j |
| Ex. 3 | (R) | $CH_2OCH_3$ | Ph (m-F) | 150–151 | 6.9 [0.25] (6.1–8.0) | 46.3 [0.25] (40.4–54.5) | 6.7 | 6.9 [0.5] (4.3–9.9) | >396 [0.5] | >57.7 |
| Ex. 4 | (R) | $CH_2OCH_3$ | Ph (p-F) | 144–145 | 4.2 [0.5] (3.5–5.1) | 27.8 [0.25] (22.4–33.5) | 6.6 | 2.6 [2] (1.9–3.6) | >125, <250 | j |
| Comp. Ex. 4 | (R, S) | $OCH_3$ | Ph | 145–146 | 98.30 | >100 <300 | >1, <3 | —[j] | j | j |
| Comp. Ex. 6 | (R) | furyl | Ph | 190–197 | 3.3 | 23.8 | >.2 | —[j] | —[j] | j |
| Comp. Ex. 7 | (S) | furyl | Ph | 196–197 | >25. | >200 | | —[j] —[j] | j | j |
| Comp. Ex. 5 | (R, S) | furyl | Ph | 178–179 | 10.3 | ~40 | >3.9 | —[j] | —[j] | j |
| Comp. Ex. 13 | (D, L) | Ph | Ph | 112–115 | 20.3 | 96.92 | 4.77 | 48.3 | >1000 | >20.7 |

[a]Melting points (°C.) are uncorrected.
[b]The compounds were administered interperitoneally. $ED_{50}$ and $TD_{50}$ values are in mg/kg. Numbers in parentheses are 95% confidence intervals. The dose effect data was obtained at the "time of peak effect" [indicated in hours in the brackets].
[c]MES = maximal electroshock seizure test.
[d]Tox = neurologic toxicity determined from rotorod test.
[e]PI = protective index ($TD_{50}$/MES $Ed_{50}$)
[f]The compounds were administered orally.
[g]No ataxia observed up to 1000 mg/kg.
[j]Data not available The compounds of the present invention were compared with respect to their efficacy and toxicity and PI values to compounds having a structural similarity with the difference being the substituent at $R^2$. The protocols for these compounds is as described hereinabove.

The results thereof are provided in Table I.

As clearly shown by the above data, the R enantiomers of the present invention have quite potent anticonvulsant activity. The inventor has also found that the R stereoisomer is unexpectedly more potent than the corresponding S stereoisomer and the racemic mixture.

The data in the table clearly demonstrate that the efficacy of the comparative examples are significantly less than those of the present invention. Only the 2-furyl derivative in the Table shows comparable potency.

In addition, the compounds of the present invention have relatively low neurological toxicity, considering the efficacy thereof. In fact, as clearly shown by the data, the neurological toxicity is significantly lower in rats in which the compounds were administered orally than in the mice in which the compounds were administered intraperitoneally. In fact, in rats, the neurological toxicity of the compounds of the present invention is very low.

The PI values of the compounds of the present invention are quite high in the mice model in which the compounds were administered intraperitoneally and especially in the rat model in which the compounds were administered orally. Of the compounds tested, the PI values of the compounds of the present invention are generally higher than that of the comparative examples, except for the compound in which $R^2$ is $CH_2OH$. However, the efficacy of this latter compound is significantly less than that of compounds of the present invention.

It is important to place the data in the table in proper perspective. Looking at the data, it is quite apparent that the compounds of the present invention exhibit an excellent drug profile. On the other hand, based upon the data, except for the furyl derivatives, the other comparative compounds are significantly inferior drugs relative to the compounds of the present invention. Although in some cases, the neurological toxicity of the compounds of the comparative examples is low and the PI value is satisfactory, the data cannot be viewed in a vacuum. It is preferred that the drug not have a low potency, even if it has a low neurological toxicity. After all, the objective is to administer as little drug as possible to obtain an efficacious result; the more drug administered to achieve a particular efficacious result, the greater will be the risk that the drug would have other effects, some of which are adverse, on other bodily systems of the patient. Thus, except for the furyl derivatives, based upon the data in the table the other comparative examples have a significantly poorer drug profile relative to the compounds of the present invention.

There is thus still another factor which must be taken into consideration relating to the toxicity of the drug when administered for extended periods to the animal. Obviously, even if the drug has excellent anti-convulsant activity and an excellent PI ratio, the drug will not be useful if the drug is toxic upon chronic dosing to the patient. In the pharmaceutical industry relating to anti-convulsants, one of the standards utilized to measure a drug's toxicity to the animal is liver toxicity. The objective is to find a drug having a relatively low or substantially minimal liver toxicity.

Based upon the above data, both the furyl derivative and the compounds of the present invention have an excellent drug profile; and both could be used in acute administration. However even though the furyl compound is quite active, as will be shown hereinbelow, the furyl compound is more toxic to the animal, making it considerably less undesirable for chronic administration than the compounds of the present invention. On the other hand, the compounds of the present invention as shown hereinbelow are significantly less toxic than the furyl compound, and in fact exhibit little, if any, toxicity to the animal. Thus, the compounds of the present invention are useful for administration to the treated animal for an extended period.

The following experiments measure the effect of a representative compound of the present invention on the liver. The drug utilized is the compound of Example 1, i.e., R-N-Benzyl-2-Actamide-3-methoxypropionamide, hereinafter referred to as BAMP.

I. Short term liver study

The protocol is as follows:

Four groups of 8 rats each were treated via p.O. administration daily for 4 days with vehicle (groups 1 and 2), or 3.9 mg/kg of the compound of Example 1 (group 3) or 100 mg/kg of the compound of Example 1 (group 4). On day 5, animals in groups 2, 3 and 4 received 3.9 mg/kg of compound 1 (hereinafter "BAMP") and those in group 1 received another dose of the vehicle.

To verify that the drug was effective, all groups were tested at the time of peak effect (TPE) for drug efficacy against MES-induced tonic extension, as described hereinabove.

Following the MES test, animals in group 4 received 96.1 mg/kg dose of the compound of Example 1, a dose equal to the difference between the $ED_{50}$ and 100 mg/kg. On day 6, all groups were tested for sleep time response (time from loss to or regaining, of righting reflex) to a standard dose 100 mg/kg, i.p. of hexobarbital. The hexobarbital sleep time provides an assessment of hepatic drug metabolism. Following the performance of this test, all animal groups received the same treatment as they received on day 1. Day 7 had a similar dosing allocation except that group 2 received 100 mg/kg of BAMP. On days 8 and 9, four rats from each of the four groups were euthanized. Blood was collected in cooled tubes, allowed to clot, and then centrifuged to separate RBCs (red blood cells). The serum was frozen at $-70°$ until serum alanine aminotransferase (sALT) activity, indicative of potential liver damage, was determined. The livers were perfused in situ with ice cold saline, blotted dry, weighed, homogenized in 0.25M sucrose and centrifuged to separate endoplasmic reticulum (i.e., macrosomes) and cytosol.

The protein concentration of both of these subcellular fractions was determined by the Lowry method described in Lowry, et al., in *J. Biol Chem.* 193, 265–275, (1951) and the yield of microsomal protein calculated. The protein concentration of these two subcellular fractions provide the basis for calculation of all enzyme concentrations and activities.

Changes in a wide range of drug metabolizing enzymes known to be variously altered by drug treatments were sought. Both microsomal and cytosolic Phase I (cytochrome P450 catalyzed oxidations and quinone oxidoreductase activity, respectively) and microsomal (glucuronidation) and cytosolic (glutathione and sulfate conjugation) Phase II conjugation reactions were evaluated, in accordance with the procedure described in *Arch Biochem. Biophys,* 143, 318–329 (1971), the contents of which are incorporated by reference. BAMP showed no evidence of causing liver necrosis. Collectively, the results obtained from a battery of liver enzyme studies suggest that the liability for serious drug-drug interactions and liver toxicity is relatively low for this compound.

Since the compound showed minimal liver toxicity in a 48 hours study, a much longer study was performed over 30 days.

The methodology is as follows:

II. Five groups of Crl:CD® BR Charles River rats were each exposed to BAMP or a control substance (0.5% methylcellulose [400 Cps] aqueous solution in distilled water) according to the following dosage schedule:

Group 1—vehicle control (10 males, 10 females), 0 mg/kg/day

Group 2—low (10 males, 10 females), 10 mg/kg/day

Group 3—mid low (10 males, 10 females), 30 mg/kg/day

Group 4—mid high (10 males, 10 females), 100 mg/kg/day

Group 5—high (10 males, 10 females), 300 mg/kg/day

Exposure was by oral gavage, once daily, for a period of at least 30 consecutive days, after which all animals were sacrificed for pathologic evaluation.

All animals were weighed once prior to initiation of dosing and weekly thereafter. Food-fasted (overnight) blood samples for clinical chemistry and hematology were collected at termination. Blood samples were collected from the orbital venous plexus using carbon dioxide (mixed with oxygen) as an anesthetic.

All animals were sacrificed, at the appropriate time, by exsanguination, under barbiturate anesthesia, and all were subjected to a necropsy examination.

Clinical observations were reviewed at necropsy, and all grossly observed abnormalities were entered directly into the computerized data collection system. Adrenals, brain with brainstem, heart, kidneys, liver, ovaries, pituitary, testes with epididymides, and thyroid with parathyroids were weighted from each animal. The pituitary and thyroid with parathyroids were weighed after fixation and all of the other organs were weighed at the time of necropsy. The changes in the weight of the liver is depicted in Table 3.

As required by the protocol, histologic evaluations were conducted on liver only from all animals of Groups 1 (control) and 5 (high). All histologic findings were entered directly into the computerized data capture system. Lesions were graded as to relative severity or degree of involvement (1=minimal, 2=slight, 3=moderate, 4=moderately severe, 5=severe). In general, minimal represents the least consistently recognizable degree of any given histoniorphologic alteration, while severe would represent the most extreme degree reasonably possible, with the other three grades occupying a continuum between the two extremes. The grades are subjective, comparative evaluations, based on morphology alone and are not intended by themselves to imply any degree of functional impairment.

Results

Gross Findings—There were few gross abnormalities reported. All were frequently encountered in normal populations of rats of this strain and age; none were suggestive of any effect of treatment. The data is found in Table 2.

TABLE 2

30-DAY RANGE-FINDING ORAL TOXICITY STUDY OF BAMP IN RATS
GROSS PATHOLOGY INCIDENCE SUMMARY
TABLE INCLUDES:
SEX = ALL; GROUP = ALL; WEEKS = ALL
DEATH = ALL; SUBSET = ALL

| | | NUMBER OF ANIMALS AFFECTED | | | | | | | | | |
|---|---|---|---|---|---|---|---|---|---|---|---|
| | SEX: | MALE | | | | | FEMALE | | | | |
| ORGAN AND KEYWORD(S) OR PHRASE | GROUP: NUMBER: | 1 10 | 2 10 | 3 10 | 4 10 | 5 10 | 1 10 | 2 10 | 3 10 | 4 10 | 5 10 |
| PARATHYROID (PT) | NUMBER EXAMINED: | 10 | 10 | 10 | 10 | 10 | 10 | 10 | 10 | 10 | 10 |
| | NOT REMARKABLE: | 10 | 10 | 10 | 10 | 10 | 10 | 10 | 10 | 10 | 10 |
| ESOPHAGUS (ES) | NUMBER EXAMINED: | 10 | 10 | 10 | 10 | 10 | 10 | 10 | 10 | 10 | 10 |
| | NOT REMARKABLE: | 10 | 10 | 10 | 10 | 10 | 10 | 10 | 10 | 10 | 10 |
| TRACHEA (TR) | NUMBER EXAMINED: | 10 | 10 | 10 | 10 | 10 | 10 | 10 | 10 | 10 | 10 |
| | NOT REMARKABLE: | 10 | 10 | 10 | 10 | 10 | 10 | 10 | 10 | 10 | 10 |
| LUNG (LU) | NUMBER EXAMINED: | 10 | 10 | 10 | 10 | 10 | 10 | 10 | 10 | 10 | 10 |
| | NOT REMARKABLE: | 10 | 10 | 10 | 10 | 10 | 10 | 10 | 10 | 10 | 10 |
| HEART (HT) | NUMBER EXAMINED: | 10 | 10 | 10 | 10 | 10 | 10 | 10 | 10 | 10 | 10 |
| | NOT REMARKABLE: | 9 | 10 | 10 | 10 | 10 | 10 | 10 | 10 | 10 | 10 |
| ENLARGED | | 1 | 0 | 0 | 0 | 0 | 0 | 0 | 0 | 0 | 0 |
| SPLEEN (SP) | NUMBER EXAMINED: | 10 | 10 | 10 | 10 | 10 | 10 | 10 | 10 | 10 | 10 |
| | NOT REMARKABLE: | 10 | 10 | 10 | 10 | 10 | 10 | 10 | 10 | 10 | 10 |
| LIVER (LI) | NUMBER EXAMINED: | 10 | 10 | 10 | 10 | 10 | 10 | 10 | 10 | 10 | 10 |
| | NOT REMARKABLE: | 10 | 10 | 10 | 10 | 9 | 10 | 10 | 10 | 10 | 10 |
| ENLARGED | | 0 | 0 | 0 | 0 | 1 | 0 | 0 | 0 | 0 | 0 |

Histopathology—All were of the kinds frequently encountered in normal populations of rats of this strain and age. None presented in a dropwise pattern suggestive of a treatment effect.

TABLE 3

30-DAY RANGE-FINDING ORAL TOXICITY STUDY OF BAMP IN RATS
ORAGN WEIGHT DATA
TABLE INCLUDES:
SEX = ALL; GROUP = ALL; WEEKS = ALL
DEATH = ALL; SUBSET = ALL
LIVER

| SEX | DOSE GROUP | TERMINAL BODY WT (g) | ORGAN WEIGHT (g) | ORGAN-TO-BODY WT (%) | ORGAN-TO-BRAIN WT RATIO RT |
|---|---|---|---|---|---|
| M | 1 | | | | |
| | NUMBER IN GROUP: | 10 | 10 | 10 | 10 |
| | MEAN: | 356.3 | 11.76 | 3.323 | 5.760 |
| | STANDARD DEV: | 42.8 | 1.34 | 0.350 | 0.577 |
| M | 2 | | | | |
| | NUMBER IN GROUP: | 10 | 10 | 10 | 10 |
| | MEAN: | 342.0 | 11.10 | 3.248 | 5.388 |
| | STANDARD DEV: | 26.6 | 0.96 | 0.161 | 0.391 |
| M | 3 | | | | |
| | NUMBER IN GROUP: | 10 | 10 | 10 | 10 |
| | MEAN | 349.9 | 11.48 | 3.278 | 5.619 |
| | STANDARD DEV: | 21.4 | 1.26 | 0.265 | 0.666 |
| M | 4 | | 100 mg/kg/day × 30 days | | |
| | NUMBER IN GROUP: | 10 | 10 | 10 | 10 |
| | MEAN: | 351.5 | 11.79 | 3.351 | 5.702 |
| | STANDARD DEV: | 29.3 | 1.38 | 0.223 | 0.725 |
| M | 5 | | 300 mg/kg/day × 30 days | | |
| | NUMBER IN GROUP: | 10 | 10 | 10 | 10 |
| | MEAN: | 358.8 | 14.45* | 4.016* | 7.028* |
| | STANDARD DEV: | 28.4 | 2.24 | 0.430 | 1.141 |

| SEX | DOSE GROUP | TERMINAL BODY WT (g) | ORGAN WEIGHT (g) | ORGAN-TO-BODY WT (%) | ORGAN-TO-BRAIN WT RATIO |
|---|---|---|---|---|---|
| F | 1 | | | | |
| | NUMBER IN GROUP: | 10 | 10 | 10 | 10 |
| | MEAN: | 202.5 | 6.56 | 3.247 | 3.374 |

TABLE 3-continued

30-DAY RANGE-FINDING ORAL TOXICITY STUDY OF BAMP IN RATS
ORAGN WEIGHT DATA
TABLE INCLUDES:
SEX = ALL; GROUP = ALL; WEEKS = ALL
DEATH = ALL; SUBSET = ALL
LIVER

| | | | | | |
|---|---|---|---|---|---|
| F | STANDARD DEV: | 13.1 | 0.54 | 0.266 | 0.296 |
| | 2 | | | | |
| | NUMBER IN GROUP: | 10 | 10 | 10 | 10 |
| | MEAN: | 214.1 | 6.91 | 3.237 | 3.665 |
| | STANDARD DEV: | 12.2 | 0.76 | 0.379 | 0.440 |
| F | 3 | | | | |
| | NUMBER IN GROUP: | 10 | 10 | 10 | 10 |
| | MEAN | 207.0 | 6.71 | 3.244 | 3.453 |
| | STANDARD DEV: | 17.7 | 0.66 | 0.185 | 0.350 |
| F | 4 | | 100 mg/kg/day × 30 days | | |
| | NUMBER IN GROUP: | 10 | 10 | 10 | 10 |
| | MEAN: | 218.3 | 7.88* | 3.608 | 4.179* |
| | STANDARD DEV: | 16.7 | 1.00 | 0.310 | 0.312 |
| F | 5 | | 300 mg/kg/day × 30 days | | |
| | NUMBER IN GROUP: | 10 | 10 | 10 | 10 |
| | MEAN: | 205.9 | 7.88* | 3.832* | 4.313* |
| | STANDARD DEV: | 14.3 | 0.88 | 0.419 | 0.457 |

*significantly different from control value p ≦0.05
RT - Date analyzed following rank transformation.

Conclusions

The liver of rats exposed to BAMP by oral gavage for at least 30 days showed no histologic evidence of an adverse effect at the highest dose level employed (300 mg/kg/day). The results were compared with the comparative examples in Table I which showed the greatest efficacy and greatest PI values, viz., the compound of Comparative Example 1 (hereinafter referred to as Compound A), Comparative Example 6 (hereinafter referred to as Compound B) and Comparative Example 13 (hereinafter referred to as Compound C).

COMPARATIVE EXAMPLE 14

Compound C, i.e., N-acetyl-D, L-phenylglycine N-benzylamide was subjected to 5-day chronic treatment on anticonvulsant activity (maximal electroshock). 3 groups of 8 animals each were treated as follows. One group was given the MES $ED_{50}$ of the test drug for 5 days; the second group was given the requisite volume of the vehicle (0.04 ml/10 g body wt.) for 4 days and a single dose (MES $ED_{50}$) of the test drug on day 5; and the third group was given the requisite volume of the vehicle daily for 5 days. At the time of peak effect of the candidate substance on day 5, all groups were subjected to the MES test and the number of animals protected recorded. Seizure components of the unprotected animals were timed to the nearest 10th of a second and the extensor/flexor (E/F) ratio, S.E., and p value determined. Since extensor duration decreases and flexor duration increases as a maximal seizure is attenuated, the E/F ratio provides a measure of seizure severity.

All rats subjected to the 5-day tolerance studies were maintained in their home cage for 24 hours and then subjected to the hexobarbital sleep time test (day 6). Each rat in each of the 3 groups was given 100 mg/kg of hexobarbital (i.p.) and the sleep time measured to the nearest minute. The mean sleep time and S.E. for each group were calculated. If the mean sleep time of the treated group was significantly less than that of the treated-control group, it was considered suggestive of metabolic tolerance.

Two of the three groups of animals subjected to the hexobarbital sleep time test (chronically treated and vehicle control groups) were continued on their respective original treatment regimen for two days (days 6 and 7) and 24 hours later (day 8) subjected to liver microsomal studies. The rats were decapitated and the livers perfused with 0.9% sodium chloride solution. The livers were removed, weighed, and homogenized in 0.25M sucrose. Microsomes were prepared and their drug metabolizing capabilities (microsomal protein yield; cytochrome P-450 concentration; p-nitroanisole O-demethylase and NADPH cytochrome c reductase activities; norbenzphetamine MI complex formation; and glucuronyl transferase, erythromycin demethylase, and ethylmorphine demethylase activities) measured (Arch. Biochem. Biophys. 143: 318–329, 1971).

The chronic studies in rats demonstrate that 5 daily doses of 48 mg/kg of Compound C does not affect either the anticonvulsant activity or hexobarbital sleep time. In contrast, chronic administration of Compound C induces some liver microsomal enzyme systems as indicated by the significant increases in p-nitroanisole O-demethylase, ethylmorphine demethylase, and NADPH cytochrome c reductase activities. See Table 4.

TABLE 4

ANTICONVULSANT SCREENING PROJECT TEST RESULTS
PHASE VII EVALUATION, Rats, p.o.
CMPD C
Solvent: 30% PEG (M&P, SB)
Ave. Animal Wt: 123.3 g. TPE 4 hrs, ED50 48 mg/kg
B. EFFECT OF CHRONIC ADMINISTRATION ON THE LIVER
MICROSOMAL SYSTEM

| Parameter | Control | Treated 7 Days |
|---|---|---|
| Body Weight (g) | 148.8 ± 4.3 | 146.3 ± 3.8 |
| Liver Weight (g) | 8.36 ± 0.26 | 8.54 ± 0.26 |
| Total Protein (mg) | 30.0 ± 1.6 | 31.7 ± 1.4 |
| Cytochrome P-450 (nmoles/mg) | 0.60 ± 0.02 | 0.71 ± 0.06 |
| p-nitroanisole O-demethylase (nmoles/mg/min) | 0.56 ± 0.04 | 0.82 ± 0.12* |
| NADPH Cytochrome c reductase (nmoles/mg/min) | 137.8 ± 9.2 | 160.3 ± 5.2* |

TABLE 4-continued

ANTICONVULSANT SCREENING PROJECT TEST RESULTS
PHASE VII EVALUATION, Rats, p.o.
CMPD C
Solvent: 30% PEG (M&P, SB)
Ave. Animal Wt: 123.3 g. TPE 4 hrs, ED50 48 mg/kg
B. EFFECT OF CHRONIC ADMINISTRATION ON THE LIVER
MICROSOMAL SYSTEM

| Parameter | Control | Treated 7 Days |
|---|---|---|
| Norbenzphetamine MI Complex (nmoles/mg/min) | 0.013 ± 0.002 | 0.023 ± 0.003 |
| Glucuronyl Transferase (nmoles/mg/min) | 9.10 ± 0.20 | 9.77 ± 0.23 |
| Erythromycin demethylase (nmoles/mg/min) | 0.55 ± 0.04 | 0.64 ± 0.07 |
| Ethylmorphine demethylase (nmoles/mg/min) | 5.59 ± 0.37 | 6.75 ± 0.37* |

*Significantly different from control, p <0.05

These findings suggest that the compound C has an adverse effect on the liver.

As shown by the data, Compound C has a relatively less than desirable longterm, i.e., 7-day dose, profile in inducing liver enzyme. At 48 mg/kg/day (which is its effective one-time dose in preventing MES convulsion) p.o.×7 days, the data clearly show that hepatic involvement was observed in liver enzyme induction. It should be noted that if the MES-ED$_{50}$ dose were continued for 30 days rather than 7 days, there is a high probability that more profound changes would likely have occurred, suggesting that a safety ratio of only 1 could be anticipated in a 30-day dosing schedule.

COMPARATIVE EXAMPLE 15

Compound A, i.e., N-Acetyl-D,L-alanine-N'-benzylamide was tested for its liver toxicity in accordance with the procedure described in Comparative Example 14.

The results are as follows:

The 5-day chronic studies in rats demonstrate that 5 daily doses of 48 mg/kg does not induce tolerance to the anticonvulsant effects (MES Test) of Compound A within this period of time. This interpretation is supported by the similar effectiveness of Compound A by the MES test, the increased hexobarbital sleep time, and the unaltered liver microsomal enzyme activity. In view of the increased hexobarbital sleep time in the 5-day treated animals, it was thought important to determine the *in vitro* effect of Compound A on p-nitroanisole O-demethylase activity. The low inhibitory potency of Compound A ($I_{50}$=5000 μM) suggests that there is little interference by the compound itself on hexobarbital metabolism in the sleep test. This may indicate that the potentiation of hexobarbital sleep time is central and not peripheral. 5-day tolerance studies (MES and hexobarbital sleep time tests) and 7-day liver microsomal enzyme studies in rats, indicate that tolerance was not induced by 5 daily doses of the MES ED$_{50}$ (48 mg/kg) of Compound A (4/8 protected in the single dose acute control group; . protected in the chronically treated group); 5-day chronic treatment increased hexobarbital sleep time from that induced by a single acute dose (31.7±1.7, 34.3±1.1, and 44.4±1.9 minutes in solvent control, acute control, and 5-day treated, respectively). There was no significant change in body weight (148.8±5.9 vs 140.0±4.6 g), liver weight (7.71±0.22 vs 7.22±0.45 g), total microsomal protein (32.3±0.56±0.04 nmoles/mg), p-nitroanisole O-demethylase activity (0.50±0.04 vs 0.62±0.07 nmoles/mg/min, NADPH cytochrome c reductase activity (95.3±11.0 vs 105.0±4.1 nmoles/mg/min) in solvent control and 7-day treated, respectively. The candidate substance (Compound A) had very little inhibitory potency ($I_{50}$: c.5000 μM) for in vitro p-nitroanisole demethylation.

However, there was found little, if any liver enzyme induction in the 7-day study, and the compound was advanced to a 30 day dose ranging toxicology study, as that described hereinabove.

More specifically, 50 male and 50 female Crl:CoBs® CD(SD) selected from 68 male and 68 female rats (4 weeks old) were used as test animals in the study 1. The rats were housed individually in elevated wire mesh cages with food (Purina Certified Rodent Chow® 5002) and tap water (via an automated watering system) available ad libitum. Each batch of feed utilized was analyzed by the manufacturer for concentrations of specified heavy metals, aflatoxin, chlorinated hydrocarbons, organophosphates, and specified nutrients. The tap water was routinely analyzed on a retrospective basis for specified microorganisms, pesticides, heavy metals, alkalinity, and halogens for contamination. None were present in the animal feed or water at levels sufficient to interfere with this study.

During the quarantine and study periods, the room temperature and relative humidity were recorded twice daily and ranged from 64° to 77° F. and 12 to 51%, respectively. An artificial light cycle of 12 hours light and 12 hours dark was maintained.

The rats were selected for use on the study using a computer-generated weight randomization procedure and assigned to the following groups:

| | No. of Rats | | Compound A Dosage Levels |
|---|---|---|---|
| Group | Male | Female | mg/kg/day |
| 1 (Control) | 10 | 10 | 0 |
| 2 (low) | 10 | 10 | 30 |
| 3 (Mid-1) | 10 | 10 | 100 |
| 4 (Mid-2) | 10 | 10 | 300 |
| 5 (High) | 10 | 10 | 1000 |

Following randomization, the rats were identified with an ear tag bearing a unique permanent identification number. The rats were randomly assigned to treatment groups by first eliminating the ones with extreme body weights (±2 standard deviations from the mean body weight). Body weights at initiation ranged from 188.9 to 215.4 grams for the males and 141.8 to 158.8 grams for the females.

Compound Preparation and Administration

The desired amount of carboxymethyl cellulose was weighed on an appropriate (milligram) balance, transferred to a precalibrated beaker containing two-thirds of the total value of distilled water, and stirred on a magnetic stirrer until a solution formed. Distilled water was then added to final volume and stirred to achieve a 0.5% w/v solution.

Compound A was first ground into a powder. The desired amount for each dose level as weighed on an appropriate (milligram) balance and transferred into a precalibrated beaker. A small amount (0.5 to 4ml) of 0.5% carboxymethyl cellulose was added to Compound A and mixed to form a paste. Carboxymethyl cellulose (0.5%) was added to the final volume and mixed with a Tekmar® Tissumizer® for 2 to 3 minutes then mixed with a magnetic stirrer for 2 to 3 minutes. Fresh suspensions of Compound A were prepared daily and fresh solutions of 0.5% carboxymethyl cellulose were prepared weekly and stored refrigerated.

Each rat received Compound A at a dosage factor of 10 milliliters per kilogram of body weight via gavage between 9 a.m. and noon each day. The dosing volume for each rat was calculated and adjusted weekly by the computer from the most recently recorded individual body weight.

Compound A was administered orally.

Reserve samples of carboxymethyl cellulose (1 gram), distilled water (10 milliliters), and Compound A (1 Gram) were taken at initiation and stored at room temperature.

All rats were observed twice daily for mortality and moribundity. Clinical observations were made prior to dosing and at 1 and 4 hours after dosing. All signs were recorded as they were observed. Individual body weights were recorded at initiation of treatment, at weekly intervals, and at termination while food consumption was recorded weekly.

Sacrifice and Gross Pathology

Following 30 or 31 days of treatment, surviving rats were weighed, anesthetized, and exsanguinated under sodium pentobarbital anesthesia. Complete necropsies were performed on each rat by appropriately trained personnel using procedures approved by board-certified pathologists. Necropsy included examination of the following:

External surface
All orifices
Cranial cavity
Carcass
External surface of the brain and spinal cord (postfixation)
Nasal cavity and paranasal sinuses
Thoracic, abdominal, and pelvic cavities and their viscera
Cervical tissues and organs
All findings were recorded.

Gross Pathology

Individual gross pathology findings are as follows:

A possible compound-related effect on the kidneys was observed. Dilated pelves were noted in three males and two females in Group 5, one male each in Groups 3 and 4, and one female in Group 1. Other observations noted which appear to be incidental and not compound-related included dark areas on the lungs, liver, thymus, stomach, and cecal mucose, granular spleen, raised area on the liver, fluid-distended uterus, fluid in the cranial cavity, and a small, soft testis.

Organ Weights and Organ/Body Weight Ratios

Various organs were weighted and compared to the control, e.g., brain with stem, heart, spleen, kidney, liver, sex organs. Only the liver weights were significantly different from the control value as shown in Table 5.

TABLE 5

PATH/TOX SYSTEM OUTPUT
THIRTY-DAY DOSE RANGE FINDING STUDY OF COMPOUND A IN RATS
ORGAN TO TERMINAL BODY WEIGHT RATIO MEANS (%)
TABLE INCLUDES:
SEX = ALL; GROUP = ALL; WEEKS = ALL
DEATH = ALL; SUBSET = ALL

| SEX: | MALE | | | | | FEMALE | | | | |
|---|---|---|---|---|---|---|---|---|---|---|
| GROUP: | 1 | 2 | 3 | 4 | 5 | 1 | 2 | 3 | 4 | 5 |
| NUMBER: | 10 | 10 | 10 | 10 | 10 | 10 | 10 | 10 | 10 | 10 |
| BR - BRAIN W/STEM | | | | | | | | | | |
| # IN GRP: 10 | 10 | 10 | 10 | 10 | 10 | 10 | 10 | 10 | 10 |
| MEAN: .588 | .593 | .599 | .581 | .571 | .918 | .887 | .899 | .934 | .891 |
| STAND DEV: .034 | .065 | .037 | .019 | .035 | .048 | .043 | .044 | .073 | .079 |
| HT - HEART | | | | | | | | | | |
| # IN GRP: 10 | 10 | 10 | 10 | 10 | 10 | 10 | 10 | 10 | 10 |
| MEAN: .321 | .313 | .314 | .328 | .343 | .358 | .372 | .345 | .373 | .347 |
| STAND DEV: .027 | .021 | .037 | .055 | .057 | .029 | .039 | .035 | .028 | .033 |
| SP - SPLEEN | | | | | | | | | | |
| # IN GRP: 10 | 10 | 10 | 10 | 10 | 10 | 10 | 10 | 10 | 10 |
| MEAN: .176 | .172 | .166 | .163 | .176 | .200 | .204 | .200 | .198 | .189 |
| STAND DEV: .029 | .027 | .020 | .013 | .021 | .034 | .022 | .021 | .036 | .016 |
| KD - KIDNEY | | | | | | | | | | |
| # IN GRP: 10 | 10 | 10 | 10 | 10 | 10 | 10 | 10 | 10 | 10 |
| MEAN: .732 | .719 | .694 | .695 | .770 | .753 | .773 | .768 | .770 | .763 |
| STAND DEV: .038 | .043 | .055 | .047 | .063 | .063 | .063 | .043 | .043 | .054 |
| LI - LIVER | | | | | | | | | | |
| # IN GRP: 10 | 10 | 10 | 10 | 10 | 10 | 10 | 10 | 10 | 10 |
| MEAN: 2.846 | 2.849 | 3.059* | 3.101* | 3.683* | 3.004 | 3.122 | 3.166 | 3.172 | 3.739* |
| STAND DEV: .183 | .167 | .238 | .147 | .173 | .249 | .211 | .147 | .167 | .242 |
| TP - TESTIS/EPIDID | | | | | | | | | | |
| # IN GRP: 10 | 10 | 10 | 10 | 10 | 0 | 0 | 0 | 0 | 0 |
| MEAN: 1.251 | 1.265 | 1.219 | 1.212 | 1.202 | | | | | |
| STAND DEV: .171 | .118 | .136 | .098 | .099 | | | | | |

*Significantly different from the control value, (p $\leq$ .05).

Thus, the mean liver weight was increased in the males of Groups 4, (300 mg/kg/day×30 days) and 5 (1000 mg/kg/day×30 days) in the Group 5 females. This was reflected by increases in the liver/body weight ratios. The liver/body weight ratio was also noted for the Group 3 (100 mg/kg/day×30 days) males. The only other change of note was a small increase in the mean kidney weight of the Group 5 males.

Thus, using a daily dose of 100 mg/kg as a threshold dose to a potentially hepatotoxic dose, this would give a liver safety ratio against the anti-convulsant dose of 2.1.

COMPARATIVE EXAMPLE 16

Compound C, i.e., D-(−)-α-acetamido-N-benzyl-2-furanacetylamide was evaluated for liver toxicity using the procedures described hereinabove. More specifically, various dosages such as 25 mg/kg, 100 mg/kg, 500 mg/kg of the drug was administered by oral gavage to rats for a set period of time. The rats were housed separately. The rats were periodically viewed for mortality and moribundity. At the termination of the study, the surviving rats were anesthetized, and exsanguinated under anesthesia. Complete necropsies were performed by appropriately trained personnel using procedures approved by board certified pathologists and the results were recorded.

When the D-furyl derivative of Comparative Example 6 was administered to the rat, hepatocellular necrosis was evident at 100 and 25 mg/kg in rats treated for 13 weeks.

The data respecting these compounds tested BAMP, compounds A, B and C are summarized in Table 6.

Moreover, the PI ratio of BAMP is significantly greater than that of Compounds A and C.

However, and most importantly, BAMP had no histopathologic indications at the higher dose (300 mg/kg/day for 30 days) and exhibited a minor deviation at the lower dosage. This is in complete contrast to the liver pathology of Compounds A, C and especially B. All of the comparative examples showed significantly greater liver toxicity than BAMP. This is seen in the safety ratio daily dose of MES, shown in the last column in the table. In this table, the daily dose given for multiple consecutive days at which the first indications of liver toxicity is noted. That ratio, expressed against the oral anticonvulsant MES single dose, is a safety index for onset of liver problems upon chronic administration of drug. As shown in the table, the safety ratio for the dose to signs of liver enlargement following 30 days medication relative to an oral anti-convulsant dose was 2.1 for Compound A, but was 25.6 for BAMP. For histologic signs of liver toxicity, including, for example, hepatocellular necrosis, the safety ratio was 12.7 for Compound B. In contrast, 30 days chronic dosing with BAMP caused no adverse histologic effects at 76.9 times its anti-convulsant dose.

Thus, the toxicity of the compounds of the present invention when administered for extended periods to the animal is an important parameter. Even when an anti-convulsant has active efficacy, if it shows toxicity to the animal, it is unlikely that it will be a candidate for use in chronic dosing. Thus, in selecting an anti-convulsant it is not only important that it satisfies the three criteria outlined hereinabove (high efficiency, low neurological toxicity, high P.I.) but also the

TABLE 6

| | MOUSE | | | | | RAT | | | |
| --- | --- | --- | --- | --- | --- | --- | --- | --- | --- |
| | anticonvulsant dose | | | anticonvulsant dose | | | Liver Pathology oral, multiple doses | | Safety |
| | Route i.p. $ED_{50}$ (95% C.L.) mg/kg | | Ratio to MES | Oral $ED_{50}$ (95% C.L.) mg/kg | | Ratio to | | | Ratio daily dose; MES |
| | MES | Neurotox | (p.2) | MES | Neurotox | MES | Dose | Pathology Report | (p.2) |
| Compound C D.L-phenyl | 20.3 (16.8–24.5) | 96.9 (79.8–118) | 4.8 | 48.3 (31.3–68) | >1000 | 20.7 | 48 mg/kg/day × 7 days | liver enzme induction | =1 |
| Compound A D,L methyl | 76.5 (66.6–89.0) | 454 (417–501) | 5.9 | 48.2 (32.0–71.8) | >1000 | 20.8 | 100 mg/kg/day × 30 days | liver to body wt. ratio increased male | 2.1 |
| | | | | | | | 300 mg/kg/day × 30 days | absolute weight liver inc. - male | =6.3 |
| Compound B D-furan | 3.3 (2.8–3.9) | 23.8 (17.2–30.7) | 7.2 | 1.97 (1.07–3.3) | 333 (259–411) | 175 | 25 mg/kg/day × 30 days | hepatocellular necrosis | 12.7 |
| BAMP D-methoxy-methyl | 4.46 (3.72–5.46) | 26.8 (25.5–28.0) | 6.0 | 3.90 (2.58–6.20) | >500 | >128 | 100 mg/kg/day × 30 days | liver to brain wt. ratio increased - female | 25.6 |
| | | | | | | | 300 mg/kg day × 30 days | no adverse histologic effects | >76.9 |

MES - Maximal Electroshock Seizure test
Neurotox - rotorod test. determined at peak effect As clearly, shown by the data in Table 6, the $ED_{50}$ value in the MES test for BAMP is significantly less (significantly more effective) than that of Compounds A and C and is of the same order of magnitude with respect to Compound B.

fourth criteria, low toxicity. The compounds of the present invention meet these criteria.

Thus, as clearly shown by the data the compounds of the present invention have low liver toxicity required of drugs to be used in chronic administration and are thus quite safe. The compounds of the present invention exhibit none or minimal effects on the liver.

Thus, the compounds of the present invention exhibit an excellent drug profile. They meet all of the four characteristics outlined heretofore, high potency, low neurological toxicity relative to its potency, high protective index and minimal liver toxicity. The compounds of the present invention are substantially non-toxic to the liver. These compounds of the present invention exhibit advantages that have not heretofore been realized. They therefore can be used in a treatment regimen requiring administration thereof over extended periods of time (chronic administration).

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed is:

1. A compound in the R configuration having the formula:

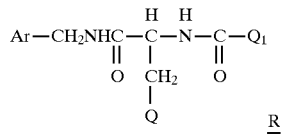

wherein
Ar is phenyl which is unsubstituted or substituted with at least one halo group;
Q is lower alkoxy, and
$Q_1$ is methyl.

2. The compound according to claim 1 which is substantially enantiopure.

3. The compound according to claim 1 wherein Q is lower alkoxy containing 1–3 carbon atoms.

4. The compound according to claim 3 wherein Q is methoxy.

5. The compound according to claim 1 wherein Ar is unsubstituted phenyl.

6. The compound according to claim 1 wherein halo is fluoro.

7. The compound according to claim 1 wherein Q is alkoxy containing 1–3 carbon atoms and Ar is unsubstituted phenyl.

8. The compound according to claim 1 which is (R)-N-Benzyl 2-Acetamido-3-methoxypropionamide.

9. The compound according to claim 8 which contains at least 90% (w/w) R stereoisomer.

10. A therapeutic composition comprising an anticonvulsant effective amount of a compound according to any one of claims 1–9 and a pharmaceutical carrier therefor.

11. A method of treating central nervous system disorders in an animal comprising administering to said animal in need thereof an anticonvulsant effective amount of a compound according to any one of claims 1–9.

12. The method according to claim 11 wherein the animal is a mammal.

13. The method according to claim 12 wherein the mammal is a human.

* * * * *

UNITED STATES PATENT AND TRADEMARK OFFICE
CERTIFICATE OF CORRECTION

PATENT NO.  : 5,773,475
DATED       : June 30, 1998
INVENTOR(S) : Harold Kohn

It is certified that error appears in the above-identified patent and that said Letters Patent is hereby corrected as shown below:

Column 3,
Line 6: "close" should read -- dose --

Column 7,
Line 62: "acctic anhydide" should read -- acetic anhydride --
Lines 66 & 67: "emantiomer" should read -- enantiomer --

Column 12,
Line 58: "Cl $_1$" should read -- $C_1$ --

Column 13,
Line 11: "62.05" should read -- δ 2.05 --
Line 24: "Mr" should read -- $M_r$ --
Line 26: "H, $_7$" should read -- H $_{17}$ --
Line 43: "cm $^-$ "should read" -- cm $^{-1}$ --
Line 53: "2C $_3$ ." should read -- $2C_3$ , --

Column 14,
Line 15: "12.00" should read -- 12.0 --
Line 20: "Mr" should read -- $M_r$ --
Line 40: "was" should read -- was --
Line 51: "actonitrile" should read -- acetonitrile --

Column 15,
Line 11: "tetrahdrofuran" should read -- tetrahydrofuran --

Column 16,
Line 33: " -35.3 -- should read -- = 35.3 --
Line 59: "Rf" should read -- $R_f$ --
Line 66: "2C $_3$ ") should read -- 2C $_3$ '" --

Column 17,
Line 11: "a" should read -- α --
Line 15: "a-acetamido" should read -- α -- acetamido --

Column 18,
Line 34 & 61: "Mr" should read -- $M_r$ --

UNITED STATES PATENT AND TRADEMARK OFFICE
CERTIFICATE OF CORRECTION

PATENT NO. : 5,773,475
DATED : June 30, 1998
INVENTOR(S) : Harold Kohn

It is certified that error appears in the above-identified patent and that said Letters Patent is hereby corrected as shown below:

Column 21,
Line 7, Table 1: "89.0" should read -- 89.0) --
Line 40, Table 1: "g No" should read -- $^h$ No --

Column 22,
Line 6, Table 1: "24.2" should read -- 48.2"

Column 23,
Line 28: "Actamide" should read -- Acetamide --

Column 26,
Line 60, Table 3: "2.24" should read -- 2.25 --

Column 27,
Line 20, Table 3: "16.7" should read -- 18.7 --
Line 26, Table 3: "Date" should read -- Data --

Column 29,
Line 53: "5-day tolerance..." should begin a new paragaraph.
Line 57: "group; protected" should read -- group; 3/8 protected --

Signed and Sealed this

Twenty-seventh Day of November, 2001

Attest:

NICHOLAS P. GODICI
Attesting Officer  Acting Director of the United States Patent and Trademark Office

UNITED STATES PATENT AND TRADEMARK OFFICE
CERTIFICATE OF CORRECTION

PATENT NO.    : 5,773,475  
DATED         : June 30, 1998  
INVENTOR(S)   : Harold Kohn It is certified that error appears in the above-identified patent and that said Letters Patent is hereby corrected as shown below:

Title page,
After Item [54], insert the following:
-- This invention was made with Government support under Grant/Contract No. NIH NS 15604 awarded by the National Institutes of Health.
The Government has certain rights in the invention. --

Signed and Sealed this

Thirtieth Day of September, 2003

JAMES E. ROGAN
*Director of the United States Patent and Trademark Office*